(12) United States Patent
Zaveri et al.

(10) Patent No.: US 9,849,025 B2
(45) Date of Patent: Dec. 26, 2017

(54) BRAIN COOLING SYSTEM

(71) Applicants:Yale University, New Haven, CT (US); The University of North Carolina at Charlotte, Charlotte, NC (US); ITN Energy Systems, Inc., Littleton, CO (US)

(72) Inventors: Hitten P Zaveri, New Haven, CT (US); Dennis D Spencer, Woodbridge, CT (US); Bharat Joshi, Pineville, CT (US); David M Binkley, Knoxville, TN (US); Bruce Lanning, Littleton, CO (US); Mohan S Misra, Golden, CO (US)

(73) Assignees: YALE UNIVERSITY, New Haven, CT (US); THE UNIVERSITY OF NORTH CAROLINA AT CHARLOTTE, Charlotte, NC (US); ITN ENERGY SYSTEMS, INC, Littleton, CO (US)

( * ) Notice: Subject to any disclaimer, the term of this patent is extended or adjusted under 35 U.S.C. 154(b) by 237 days.

(21) Appl. No.: 14/425,950

(22) PCT Filed: Sep. 7, 2013

(86) PCT No.: PCT/US2013/058646
§ 371 (c)(1),
(2) Date: Mar. 4, 2015

(87) PCT Pub. No.: WO2014/039925
PCT Pub. Date: Mar. 13, 2014

(65) Prior Publication Data
US 2015/0223971 A1    Aug. 13, 2015

Related U.S. Application Data

(60) Provisional application No. 61/698,100, filed on Sep. 7, 2012.

(51) Int. Cl.
*A61F 7/00* (2006.01)
*A61N 1/378* (2006.01)
(Continued)

(52) U.S. Cl.
CPC ............ *A61F 7/007* (2013.01); *A61B 5/0478* (2013.01); *A61B 5/4836* (2013.01); *A61F 7/12* (2013.01);
(Continued)

(58) Field of Classification Search
CPC ................. A61F 2007/0075; A61F 2007/0076
See application file for complete search history.

(56) References Cited

U.S. PATENT DOCUMENTS

| | | |
|---|---|---|
| 4,585,002 A | 4/1986 | Kissin |
| 5,829,876 A | 11/1998 | Schwartz et al. |

(Continued)

*Primary Examiner* — Kaitlyn Smith
(74) *Attorney, Agent, or Firm* — Welsh Flaxman & Gitler LLC

(57) ABSTRACT

A clinical grid electrode system for seizure control through local cooling, mapping brain function and me provision of reversible functional ablation. The system includes a modular, scalable, cooling and sensing array composed of a plurality of cooling sensing elements. The system also includes a control system to which die cooling and sensing array is coupled for providing for control and monitoring of die cooling sensing elements making up the cooling and sensing array.

25 Claims, 9 Drawing Sheets

(51) Int. Cl.
   *A61N 1/36*      (2006.01)
   *A61N 1/365*     (2006.01)
   *A61B 5/0478*    (2006.01)
   *A61B 5/00*      (2006.01)
   *A61F 7/12*      (2006.01)

(52) U.S. Cl.
   CPC ....... *A61N 1/36025* (2013.01); *A61N 1/3655* (2013.01); *A61N 1/36064* (2013.01); *A61N 1/3787* (2013.01); *A61F 2007/126* (2013.01)

(56) References Cited

U.S. PATENT DOCUMENTS

| | | | |
|---|---|---|---|
| 5,871,526 | A | 2/1999 | Gibbs et al. |
| 6,248,126 | B1 | 6/2001 | Lesser et al. |
| 6,366,813 | B1 | 4/2002 | DiLorenzo |
| 6,549,804 | B1 | 4/2003 | Osorio et al. |
| 6,629,990 | B2 | 10/2003 | Putz et al. |
| 6,793,670 | B2 | 9/2004 | Osorio et al. |
| 6,819,956 | B2 | 11/2004 | DiLorenzo |
| 6,882,881 | B1 * | 4/2005 | Lesser ............... A61F 7/12 607/3 |
| 6,978,183 | B2 * | 12/2005 | Rothman ............... A61F 7/12 600/544 |
| 7,146,211 | B2 | 12/2006 | Frei et al. |
| 7,162,303 | B2 | 1/2007 | Levin et al. |
| 7,164,077 | B2 | 1/2007 | Venkatasubramanian |
| 7,204,833 | B1 | 4/2007 | Osorio et al. |
| 7,212,851 | B2 | 5/2007 | Donoghue et al. |
| 7,228,171 | B2 | 6/2007 | Lesser et al. |
| 7,277,748 | B2 | 10/2007 | Wingeier et al. |
| 7,280,870 | B2 | 10/2007 | Nurmikko et al. |
| 7,313,440 | B2 | 12/2007 | Miesel |
| 7,324,851 | B1 | 1/2008 | DiLorenzo |
| 7,330,760 | B2 | 2/2008 | Heruth et al. |
| 7,341,562 | B2 | 3/2008 | Pless et al. |
| 7,346,312 | B2 | 3/2008 | Irazoqui-Pastor et al. |
| 7,447,545 | B2 | 11/2008 | Heruth et al. |
| 7,616,990 | B2 | 11/2009 | Chavan et al. |
| 7,617,005 | B2 | 11/2009 | Demarais et al. |
| 7,623,928 | B2 | 11/2009 | DiLorenzo |
| 7,653,438 | B2 | 1/2010 | Deem et al. |
| 7,717,948 | B2 | 5/2010 | Demarais et al. |
| 7,747,325 | B2 | 6/2010 | DiLorenzo |
| 7,792,583 | B2 | 9/2010 | Miesel et al. |
| 7,819,812 | B2 | 10/2010 | John et al. |
| 7,894,905 | B2 | 2/2011 | Pless et al. |
| 7,896,807 | B2 | 3/2011 | Clancy et al. |
| 7,917,206 | B2 | 3/2011 | Frei et al. |
| 7,945,316 | B2 | 5/2011 | Giftakis et al. |
| 7,974,705 | B2 | 7/2011 | Zdeblick et al. |
| 7,979,130 | B2 | 7/2011 | Carlson et al. |
| 8,041,419 | B2 | 10/2011 | Giftakis et al. |
| 8,103,351 | B2 | 1/2012 | Gerber et al. |
| 8,108,033 | B2 | 1/2012 | Drew et al. |
| 8,126,561 | B2 | 2/2012 | Chavan et al. |
| 8,135,473 | B2 | 3/2012 | Miesel et al. |
| 8,145,316 | B2 | 3/2012 | Deem et al. |
| 8,165,682 | B2 | 4/2012 | Gopalsami et al. |
| 8,165,683 | B2 | 4/2012 | Carlson et al. |
| 8,165,684 | B2 | 4/2012 | Putz et al. |
| 8,190,248 | B2 | 5/2012 | Besio et al. |
| 8,267,983 | B2 | 9/2012 | Rogers et al. |
| 8,326,420 | B2 | 12/2012 | Skelton et al. |
| 8,332,024 | B2 | 12/2012 | Rapoport et al. |
| 8,337,404 | B2 | 12/2012 | Osorio |
| 8,353,837 | B2 | 1/2013 | John et al. |
| 8,364,272 | B2 | 1/2013 | Goetz |
| 8,380,314 | B2 | 2/2013 | Panken et al. |
| 8,382,667 | B2 | 2/2013 | Osorio |
| 8,417,344 | B2 | 4/2013 | Colborn et al. |
| 8,428,733 | B2 | 4/2013 | Carlson et al. |
| 8,447,401 | B2 | 5/2013 | Miesel et al. |
| 8,457,744 | B2 | 6/2013 | Janzig et al. |
| 8,457,750 | B2 | 6/2013 | Gerber et al. |
| 8,463,377 | B2 | 6/2013 | Maskara et al. |
| 8,485,979 | B2 | 7/2013 | Giftakis et al. |
| 8,504,150 | B2 | 8/2013 | Skelton |
| 8,515,549 | B2 | 8/2013 | Panken et al. |
| 8,515,550 | B2 | 8/2013 | Skelton et al. |
| 8,525,016 | B2 | 9/2013 | Deane et al. |
| 8,527,039 | B2 | 9/2013 | Carlson et al. |
| 8,538,512 | B1 | 9/2013 | Bibian et al. |
| 8,538,537 | B2 | 9/2013 | Hulvershorn et al. |
| 8,543,199 | B2 | 9/2013 | Snyder et al. |
| 8,543,214 | B2 | 9/2013 | Osorio et al. |
| 8,562,523 | B2 | 10/2013 | Osorio |
| 8,562,524 | B2 | 10/2013 | Osorio |
| 8,562,536 | B2 | 10/2013 | Osorio et al. |
| 8,565,864 | B2 | 10/2013 | Drew et al. |
| 8,565,886 | B2 | 10/2013 | Nelson et al. |
| 8,579,786 | B2 | 11/2013 | Osorio et al. |
| 8,579,834 | B2 | 11/2013 | Davis et al. |
| 8,583,239 | B2 | 11/2013 | Pless et al. |
| 8,583,252 | B2 | 11/2013 | Skelton et al. |
| 8,591,562 | B2 | 11/2013 | D'Ambrosio et al. |
| 8,594,798 | B2 | 11/2013 | Osorio et al. |
| 8,600,512 | B2 | 12/2013 | Whitehurst et al. |
| 8,600,521 | B2 | 12/2013 | Armstrong et al. |
| 8,615,309 | B2 | 12/2013 | Craig |
| 8,630,715 | B2 | 1/2014 | Goetz et al. |
| 8,641,646 | B2 | 2/2014 | Colborn |
| 8,644,919 | B2 | 2/2014 | Zdeblick |
| 8,644,945 | B2 | 2/2014 | Skelton et al. |
| 8,649,871 | B2 | 2/2014 | Frei et al. |
| 8,652,189 | B2 * | 2/2014 | Gafni ............... A61B 5/0484 606/20 |
| 8,660,648 | B2 | 2/2014 | Chavan et al. |
| 8,660,666 | B2 | 2/2014 | Craig |
| 8,670,830 | B2 | 3/2014 | Carlson et al. |
| 8,684,921 | B2 | 4/2014 | Osorio |
| 8,684,998 | B2 | 4/2014 | Demarais et al. |
| 8,688,221 | B2 | 4/2014 | Miesel et al. |
| 8,688,225 | B2 | 4/2014 | Panken et al. |
| 8,706,181 | B2 | 4/2014 | Stypulkowski et al. |
| 8,706,237 | B2 | 4/2014 | Giftakis et al. |
| 8,708,934 | B2 | 4/2014 | Skelton et al. |
| 8,712,539 | B2 | 4/2014 | Goetz et al. |
| 8,725,239 | B2 | 5/2014 | Liao |
| 8,725,243 | B2 | 5/2014 | DiLorenzo et al. |
| 8,725,244 | B2 | 5/2014 | Miesel et al. |
| 8,728,137 | B2 | 5/2014 | Zarins et al. |
| 8,728,138 | B2 | 5/2014 | Zarins et al. |
| 8,734,499 | B2 | 5/2014 | Lovett et al. |
| 8,738,136 | B2 | 5/2014 | Frei et al. |
| 8,738,139 | B2 | 5/2014 | Lanning et al. |
| 8,738,154 | B2 | 5/2014 | Zdeblick et al. |
| 8,744,562 | B2 | 6/2014 | Giftakis et al. |
| 8,751,011 | B2 | 6/2014 | Skelton et al. |
| 8,755,901 | B2 | 6/2014 | Skelton et al. |
| 8,758,274 | B2 | 6/2014 | Sahasrabudhe et al. |
| 8,761,868 | B2 | 6/2014 | Giftakis et al. |
| 8,761,889 | B2 | 6/2014 | Wingeier et al. |
| 8,761,890 | B2 | 6/2014 | Gupta et al. |
| 8,762,065 | B2 | 6/2014 | DiLorenzo |
| 8,768,447 | B2 | 7/2014 | Ermes et al. |
| 8,768,471 | B2 | 7/2014 | Colborn et al. |
| 8,771,194 | B2 | 7/2014 | John et al. |
| 8,774,937 | B2 | 7/2014 | Mercanzini et al. |
| 8,781,597 | B2 | 7/2014 | DiLorenzo |
| 8,784,463 | B2 | 7/2014 | Zarins et al. |
| 8,786,624 | B2 | 7/2014 | Echauz et al. |
| 8,788,042 | B2 | 7/2014 | Mercanzini et al. |
| 8,788,055 | B2 | 7/2014 | Gerber et al. |
| 8,788,064 | B2 | 7/2014 | Mercanzini et al. |
| 8,792,982 | B2 | 7/2014 | Miesel et al. |
| 8,798,754 | B2 | 8/2014 | Knudson et al. |
| 8,805,520 | B2 | 8/2014 | Pless et al. |
| 8,812,099 | B2 | 8/2014 | Asirvatham et al. |
| 8,812,117 | B2 | 8/2014 | Gerber et al. |
| 8,849,407 | B1 * | 9/2014 | Danilov ............... A61N 1/0492 607/134 |
| 2004/0111042 | A1 | 6/2004 | Szabo et al. |
| 2004/0111043 | A1 | 6/2004 | Szabo et al. |

(56) References Cited

U.S. PATENT DOCUMENTS

| | | |
|---|---|---|
| 2004/0133119 A1 | 7/2004 | Osorio et al. |
| 2005/0215916 A1 | 9/2005 | Fadem et al. |
| 2006/0173364 A1 | 8/2006 | Clancy et al. |
| 2006/0293578 A1 | 12/2006 | Rennaker |
| 2007/0010860 A1* | 1/2007 | Gafni .................. A61B 5/0484 607/96 |
| 2008/0077039 A1 | 3/2008 | Donnett et al. |
| 2008/0243022 A1 | 10/2008 | Donnett et al. |
| 2009/0112273 A1 | 4/2009 | Wingeier et al. |
| 2009/0112277 A1 | 4/2009 | Wingeier et al. |
| 2009/0149913 A1 | 6/2009 | Putz et al. |
| 2009/0240314 A1 | 9/2009 | Kong et al. |
| 2010/0106041 A1 | 4/2010 | Ghovanloo et al. |
| 2010/0312318 A1 | 12/2010 | D'Ambrosio et al. |
| 2011/0092842 A1 | 4/2011 | Decaria et al. |
| 2012/0022391 A1 | 1/2012 | Leuthardt |
| 2012/0116475 A1 | 5/2012 | Nelson et al. |
| 2012/0123289 A1 | 5/2012 | Sorenson et al. |
| 2012/0191157 A1 | 7/2012 | Stypulkowski et al. |
| 2012/0203129 A1 | 8/2012 | Rennaker, II |
| 2012/0209346 A1 | 8/2012 | Bikson et al. |
| 2012/0271148 A1 | 10/2012 | Nelson |
| 2012/0271189 A1 | 10/2012 | Nelson et al. |
| 2012/0271374 A1 | 10/2012 | Nelson et al. |
| 2012/0271375 A1 | 10/2012 | Wu et al. |
| 2012/0277820 A1 | 11/2012 | Wu et al. |
| 2012/0290052 A1 | 11/2012 | D'Ambrosio et al. |
| 2012/0310298 A1 | 12/2012 | Besio et al. |
| 2013/0041296 A1* | 2/2013 | Tass .................. A61H 7/001 601/15 |
| 2013/0137955 A1 | 5/2013 | Kong et al. |
| 2013/0138176 A1 | 5/2013 | Goetz |
| 2013/0296987 A1* | 11/2013 | Rogers .................. A61F 7/007 607/112 |
| 2013/0310907 A1* | 11/2013 | Rogers .................. A61F 7/007 607/113 |
| 2014/0135870 A1 | 5/2014 | Carlson et al. |
| 2014/0155772 A1 | 6/2014 | Frei et al. |
| 2014/0163627 A1 | 6/2014 | Starr et al. |
| 2014/0180358 A1 | 6/2014 | Giftakis et al. |
| 2014/0194944 A1 | 7/2014 | Romanelli et al. |
| 2014/0194945 A1 | 7/2014 | Stypulkowski et al. |
| 2014/0200624 A1 | 7/2014 | Jaseja |
| 2014/0213926 A1 | 7/2014 | Vaidyanathan |
| 2014/0222101 A1 | 8/2014 | Miesel et al. |
| 2014/0228701 A1 | 8/2014 | Chizeck et al. |
| 2014/0235990 A1 | 8/2014 | Yoo et al. |
| 2014/0243613 A1 | 8/2014 | Osorio |
| 2014/0343374 A1* | 11/2014 | Carr .................. A61B 5/01 600/301 |

\* cited by examiner

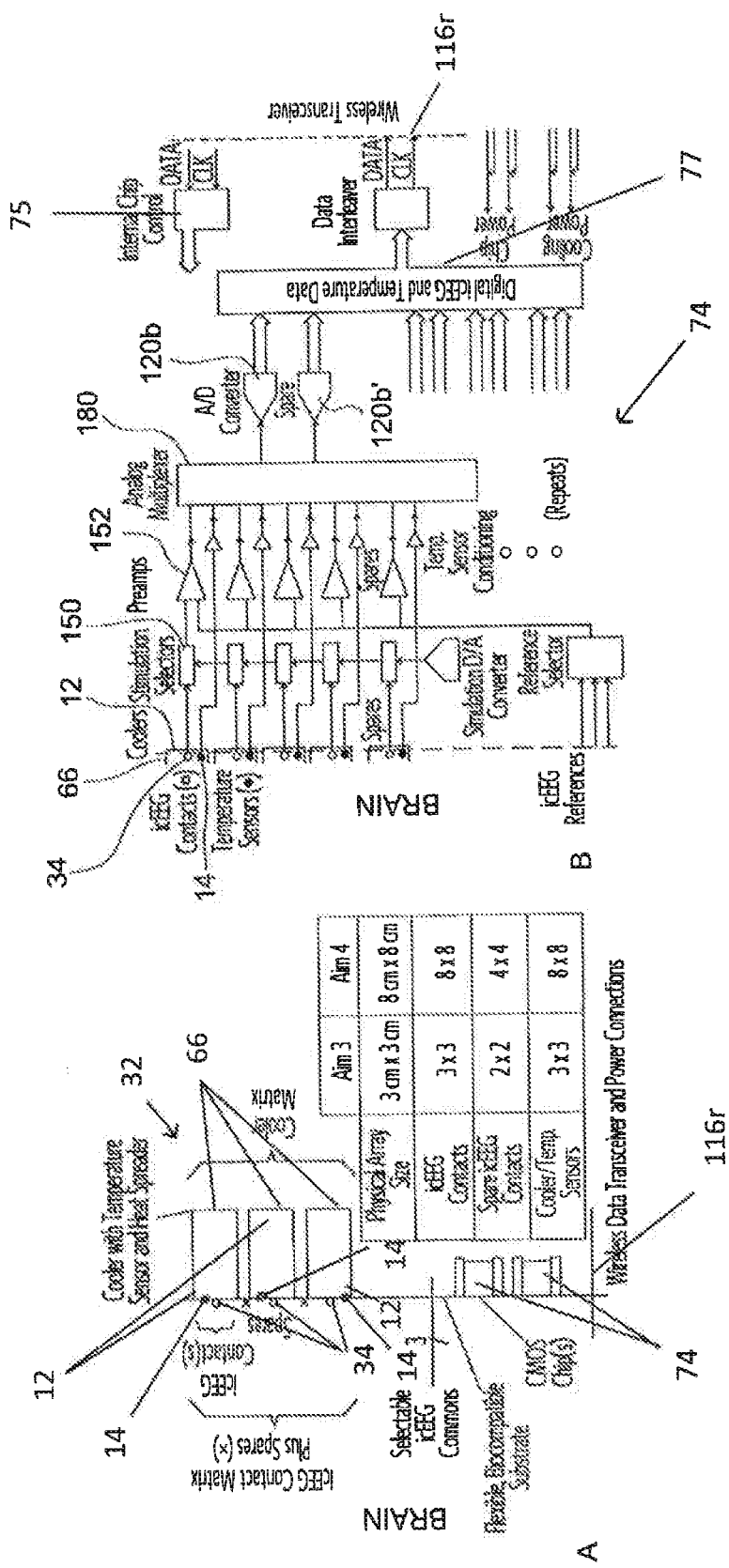

BRAIN COOLING SYSTEM

CROSS REFERENCE TO RELATED APPLICATION

This application claims the benefit of U.S. Provisional Application Ser. No. 61/698,100, entitled "BRAIN COOLING SYSTEM," filed Sep. 7, 2012.

BACKGROUND OF THE INVENTION

1. Field of the Invention

The invention relates generally to devices for treating epilepsy patients with the application of focused cooling to the brain.

2. Description of the Related Art

Accurate sensing of intracranial electrical activity, such as for determining epileptogenic foci, mapping brain function or otherwise, often may require use of a plurality of brain contacts. Epileptogenic mapping is one example of the use of electrical devices with tissue-engagement contacts. Examples of two kinds of intracranial electrical contact devices are depth probes and flexible flat surface members.

Depth probes, which may be referred to as "depth electrodes", penetrate deep into the brain tissue. On the other hand, flexible flat surface members, including what are sometimes referred to as "strip" electrodes and "grid" electrodes may be placed subdurally in direct contact with brain tissue at the surface of the brain.

Examples of such electrodes include, but are not limited to, electrodes described in U.S. Pat. No. 4,735,208 (Wyler et al.), U.S. Pat. No. 4,805,625 (Putz), U.S. Pat. No. 4,903,702 (Putz), U.S. Pat. No. 5,044,368 (Putz) and U.S. Pat. No. 5,097,835 (Putz).

Each of these different kinds of intracranial tissue-engagement electrodes is connected to some circuitry which typically captures and records the EEG (electroencephalography) signals for evaluation and analysis of various types. There is a diagnostic need for an increased number of electrodes in order to increase the precision of analysis and diagnosis based on the captured EEG information. An increase in the number of electrodes requires higher data transmission bandwidths if the full amount of data captured from the electrodes is delivered to the monitoring system electronics. Further, there is a diagnostic need to monitor patients for longer periods of time, again for increased precision of diagnosis.

In addition to the need for monitoring brain activity to further the understanding of epilepsy and control seizures, therapies are being developed. Current practice for implantable devices for seizure control is built on experience gained from several decades of intracranial EEG monitoring for epilepsy surgery. Low-level signals are passively sensed and conducted to instrumentation which is placed in the chest or the skull or at the bed-side in the case of intracranial EEG monitoring for epilepsy surgery (Limning B, Joshi B, Kyriakides T, Spencer D and Zaveri H (2011). Emerging technologies for brain implantable devices. Epilepsy: The Intersection of Neurosciences, Biology, Mathematics, Engineering and Physics, In press. I. Osorio, H. Zaveri, M. Frei and S. Arthurs, CRC Press; Lanning B, Nuebel G, Nolan J, Gomez N, Joshi B S, Misra M, Putz D, Dhaher R, Wang Y, Vives K P, Duckrow R B, Williamson A, Eid T, Spencer D D and Zaveri H P. Battery Free Wireless Transmission of Intracranial EEGs. Submitted 2011; Zaveri H and Frei M (2011). Intracranial EEC: Electrodes, filtering, amplification, digitization, storage and display. Epilepsy: The Intersection of Neurosciences, Biology, Mathematics, Engineering and Physics, In press. I. Osorio, H. Zaveri, M. Frei and S. Arthurs, CRC Press.). This methodology has a number of built-in limitations, particularly the dependence on passive sensing and the lack of scalability of the number of intracranial EEC sensors (Lanning B, Joshi B, Kyriakides T, Spencer D and Zaveri H (2011). Emerging technologies for brain implantable devices. Epilepsy: The Intersection of Neurosciences, Biology, Mathematics, Engineering and Physics, In press. I. Osorio, H. Zaveri, M. Frei and S. Arthurs, CRC Press).

However, pharmaceutical and surgical therapy for epilepsy remain inadequate, and alternative approaches such as electrical stimulation with implanted electrodes and local delivery of anti-epileptic drugs are being explored to control seizures in medically intractable epilepsy. Brain cooling has been considered for a number of decades for application to head trauma, ischemia, cancer, pain and epilepsy (Fay T. Early experiences with local and generalized refrigeration of the human brain. Journal of Neurosurgery 1959; 16 (3): 239-59; discussion 259-60; Rothman S M. The therapeutic potential of focal cooling for neocortical epilepsy. Neurotherapeutics 2009; 6 (2): 251-7; Fujii M, Fujioka H, Oku T, Tanaka N, Imoto H, Maruta Y, Nomura S, Kajiwara K, Saito T, Yamakawa T, Yamakawa T and Suzuki M. Application of focal cerebral cooling for the treatment of intractable epilepsy. Neurol Med Chir (Tokyo) 2010; 50 (9): 839-44). Multiple mechanisms have been identified for the protective aspects of hypothermia including decreased cerebral metabolism, reduction in free radicals, and anti-inflammatory effects among others (Ginsberg M and Belayev L (2005). Biological and molecular mechanisms of hypothermic neuroprotection. Therapeutic hypothermia. New York, Marcel Dekker: 85-140; Froehler M and Geocadin R. Hypothermia for neuroprotection after cardiac arrest: Mechanisms, clinical trials and patient care. Neurological Sciences 2007; 261: 118-126). It has been suggested that seizure control may occur due to change in transmitter release (Rothman S M. The therapeutic potential of focal cooling for neocortical epilepsy. Neurotherapeutics 2009; 6 (2): 251-7) or interruption of network synchronization (Javedan S P, Fisher R S, Eder H G, Smith K and Wu J. Cooling abolishes neuronal network synchronization in rat hippocampal slices. Epilepsia 2002; 43 (6): 574-80). The technical challenges of developing a brain implantable cooling device are multiple and have been documented (Osorio I, Chang F-C and Gopalsami N. Seizure control with thermal energy? Modeling of heat diffusivity in brain tissue and computer-based design of a prototype mini-cooler. Epilepsy & Behavior 2009; 16 (2): 203-11; Rothman S M. The therapeutic potential of focal cooling for neocortical epilepsy. Neurotherapeutics 2009; 6 (2): 251-7; Fujii M, Fujioka H, Oku T, Tanaka N, Imoto H, Maruta Y, Nomura S, Kajiwara K, Saito T, Yamakawa T, Yamakawa T and Suzuki M. Application of focal cerebral cooling for the treatment of intractable epilepsy. Neurol Med Chit (Tokyo) 2010; 50 (9): 839-44). While researchers have explored the possibility of controlling seizures in epilepsy patients through local in vivo cooling, a clinical device for seizure control through local cooling has not been realized and has not yet been developed. Accordingly it is an objective of the present invention to provide such a clinical device.

SUMMARY OF THE INVENTION

It is, therefore, an object of the present invention to provide a clinical grid electrode system for seizure control through local cooling, mapping brain function and the provision of reversible functional ablation. The system includes a modular, scalable, cooling and sensing array composed of a plurality of cooling sensing elements. The system also includes a control system to which the cooling and sensing array is coupled for providing for control and monitoring of the cooling sensing elements making up the cooling and sensing array.

It is also an object of the present invention to provide a system wherein each of the cooling sensing elements is composed of a cooling module, a temperature sensor and an EEG electrode.

It is another object of the present invention to provide a system wherein the cooling module includes an active thermoelectric cooling element with a fast response time, high heat pumping capacity, and small/thin footprint.

It is a further object of the present invention to provide a system wherein the cooling module also includes a phase change material based heat spreader.

It is also an object of the present invention to provide a system wherein each of the cooling sensing elements has a layered configuration with a lowermost tissue contact layer composed of the EEG electrode positioned on the cooling module, a cooling plate positioned along the lowermost tissue contact layer and to which the EEG electrode is mounted.

It is another object of the present invention to provide a system wherein a thin-film thermoelectric cooling element with a fast response time, high heat pumping capacity, and small/thin footprint is secured to a backside of the cooling plate.

It is a further object of the present invention to provide a system wherein a heat plate and a heat spreader are mounted on a side of the thin-film thermoelectric cooling element opposite the cooling plate.

It is also an object of the present invention to provide a system wherein the heat spreader is composed of a phase change material.

It is another object of the present invention to provide a system wherein the cooling module, the temperature sensor, and the EEG electrode are mounted within a film supporting structure and the temperature sensor is mounted along the film supporting structure at a position adjacent the cooling module and the EEG electrode It is another object of the present invention to provide a system wherein the control system includes electronics for power, thermoelectric element driving, temperature sensing, and signal conditioning.

It is a further object of the present invention to provide a system wherein temperature control is implemented in a steady state mode wherein the temperature of a focal part of the brain is held at a lower temperature for several seconds or minutes.

It is also an object of the present invention to provide a system wherein temperature control is implemented in a pulse control mode, wherein a focal part of the brain is rapidly cooled using one or more brief pulses each of which will last for a few seconds to tens of seconds.

It is another object of the present invention to provide a system wherein the control system includes a multiplexer, amplifier, A/D converter, microprocessor, infrared transceiver, antenna, power supply, external receiver, and external power transmitter.

It is a further object of the present invention to provide a system wherein the cooling sensing elements are connected to remote circuitry which is mounted within a body cavity adjacent the cooling and sensing array.

It is also an object of the present invention to provide a system wherein the remote circuitry includes a multiplexer that selects appropriate cooling sensing elements to be measured and/or activated.

It is another object of the present invention to provide a system wherein the multiplexer is controlled by a microprocessor.

It is a further object of the present invention to provide a system wherein the cooling sensing elements are connected by an analog switch network.

It is also an object of the present invention to provide a system wherein the analog switch network creates connections between individual electrodes and functional circuitry to provide tissue stimulation current and enable remote circuitry to measure impedance.

It is another object of the present invention to provide a cooling sensing element for a clinical grid electrode system for seizure control through local cooling, mapping brain function and the provision of reversible functional ablation. The cooling sensing element includes a cooling module, a temperature sensor, and an EEG electrode.

It is a further object of the present invention to provide a cooling sensing element wherein the cooling module includes a miniaturized active thermoelectric cooling element with a fast response time, high heat pumping capacity, and small/thin footprint.

It is also an object of the present invention to provide a cooling sensing element wherein the cooling module also includes a phase change material based heat spreader.

It is another object of the present invention to provide a cooling sensing element having a layered configuration with a lowermost tissue contact layer composed of the EEG electrode positioned on the cooling module, a cooling plate positioned along the lowermost tissue contact layer and to which the EEG electrode is mounted.

It is a further object of the present invention to provide a cooling sensing element wherein a thin-film thermoelectric cooling element with a fast response time, high heat pumping capacity, and small/thin footprint is secured to a backside of the cooling plate.

It is also an object of the present invention to provide a cooling sensing element wherein a heat plate and a heat spreader are mounted on a side of the thin-film thermoelectric cooling element opposite the cooling plate.

It is another object of the present invention to provide a cooling sensing element wherein the heat spreader is composed of a phase change material.

It is a further object of the present invention to provide a cooling sensing element wherein the cooling module, the temperature sensor, and the EEG electrode are mounted within a film supporting structure and the temperature sensor is mounted along the film supporting structure at a position adjacent the cooling module and the EEG electrode.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 9(a) and 9(b) respectively show a physical illustration of complete neural implant for aims in accordance with present invention and a block diagram of a custom CMOS chip for use in accordance with the present invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

In accordance with the present invention, and with reference to FIGS. 1 to 9, a clinical grid electrode system 10 for seizure control through local cooling is disclosed. The present grid electrode system 10 includes a modular, scalable, cooling and sensing array 32 composed of a plurality of cooling sensing elements 66. The cooling and sensing array 32 is coupled to a control system 68 providing for control and monitoring of the cooling sensing elements 66 making up the cooling and sensing array 32. As such, the present grid electrode system 10 provides for the recording of intracranial EEG and temperature signals as well as cooling selected brain areas to control seizures in humans.

The present grid electrode system 10 provides three primary functionalities considered to be of importance to those suffering from seizures and other neurological disorders. The three functionalities are controlling seizures, mapping brain function and the provision of reversible functional ablation.

With regard to the control of seizures, the present grid electrode system 10 seeks to use cooling to stop seizures. The cooling function is turned on when a seizure is detected, or when a seizure is anticipated, to interrupt the build-up of the seizure. The cooling function may also be turned on to serve as a prophylactic method, at specific times.

As for brain mapping, the present grid electrode system 10 uses cooling to reversibly turn off selected parts of the brain. By doing so the present invention will facilitate the ability to map brain function in individual patients. For example, the cortical location of speech or fine finger movements may be mapped by interrupting normal cortical function through focal cooling. It is appreciated the mapping function can help in planning surgical resection in patients who are being considered for brain surgery.

Finally, and with regard to reversible functional ablation, the present grid electrode system 10 permits the use of cooling to reversibly turn off a part of the cortex which is being considered for surgical resection. Such a procedure will be conducted prior to brain surgery. By doing so we will be able to better understand the functional consequences of a planned surgery, and better plan the surgery.

Figure 1:
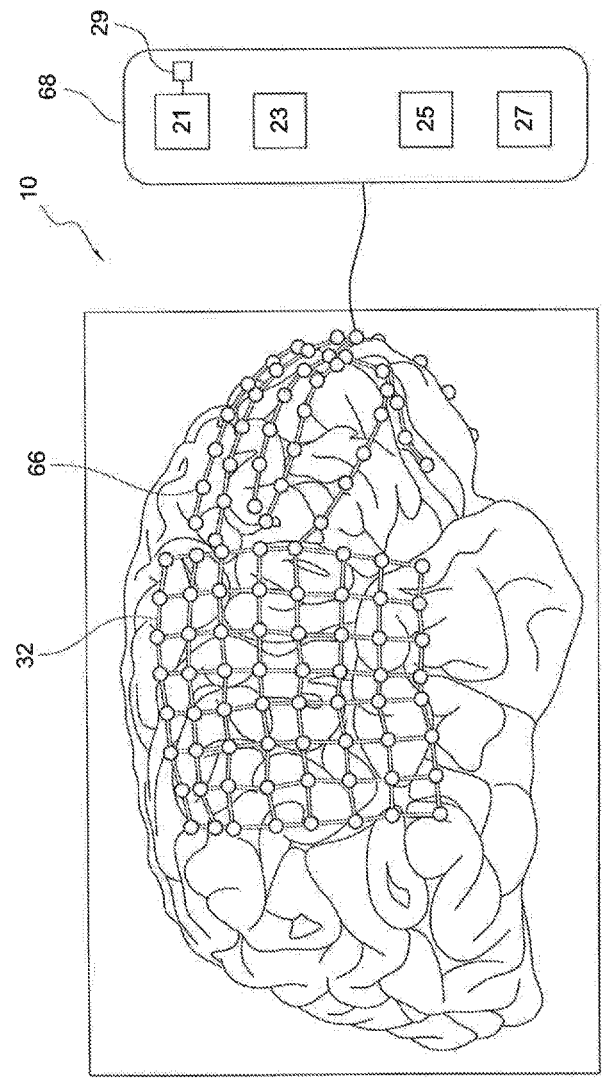
FIG. 1 is a schematic of the present grid electrode system.
Figure 2:
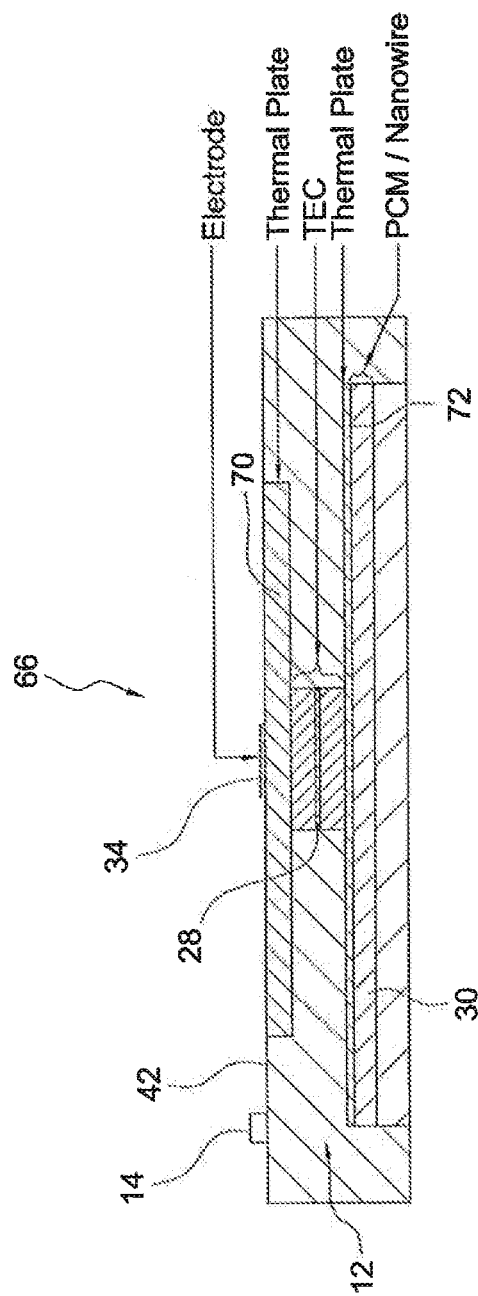
FIG. 2 is a side view of a cooling sensing element in accordance with the present invention.

With reference to FIG. 2, each of the cooling sensing elements 66 is composed of a cooling module 12, a temperature sensor 14 and an EEG electrode. 34, all associated with powerful and robust functional electronics discussed below in greater detail. Although a preferred embodiment provides the cooling sensing elements composed of a cooling module, a temperature sensor and an BEG electrode, it is appreciated it may not be necessary to provide a cooling module and temperature sensor for each EEG electrode; that is, the ratio between EEG electrodes and cooling modules/temperature sensors may not be 1:1. In some instances it may be possible that we will have more EEG electrodes than cooling modules or temperature sensors.

In particularly, and as will be discussed below in greater detail, the cooling sensing element 66 is in communication with a control system 68 including electronics for power 21 (including an on-hoard battery 29), thermoelectric element driving 23, temperature sensing 25, and signal conditioning 27. As will be appreciated based upon the following disclosure, the grid electrode system 10 offers a modular and scalable design allowing expansion into an addressable array configuration for BEG measurement and selective active cooling with unique spatial and temporal features.

The cooling module 12 includes a miniaturized active thermoelectric cooling element (thin-film cooling element) 26 with a fast response time, high heat pumping capacity, and small/thin footprint. The cooling module 12 also includes an innovative phase change material based heat spreader 30. In accordance with a preferred embodiment the thin-film thermoelectric cooling element 28 is able to cool within 10 seconds to 18° C., which is below a temperature shown to be effective for controlling seizures and brain function.

In practice, the grid electrode system 10 includes a cooling and sensing array 32 (or multiple arrays) of cooling sensing elements 66 each including a cooling module 12, a temperature sensor 14, and an EEG electrode 34. In accordance with an embodiment of the present invention, cooling and sensing arrays 32 may take various forms depending upon the specific application. For example, where it is desired to use the cooling and sensing array 32 for mapping purposes, the cooling and sensing arrays might be 8 cm×8 cm with 64 EEG electrodes, sensor modules and temperature sensors. Where the cooling and sensing array is for control purposes, small configurations, for example, 2 cm×2 cm, 2 cm×4 cm, or 3 cm×3 cm, would be more useful. It is appreciated such larger scale cooling and sensing arrays will be fundamentally the same as the smaller devices, but scaled to a larger size and with an increase in the number of thermoelectric element elements and temperature and intracranial EEG sensors.

The form factor discussed above relates to a 2 dimensional design, with EEG electrodes 34, cooling modules 12 and temperature sensors 14 placed uniformly on the support surface of the grid. A device with this form-factor would be placed on the cortex and will sense cortical signals and seek to control cortical function and dysfunction by cooling the cortex. It is also appreciated the principles underlying the present invention may be applied in a second form-factor. The second form-factor will be similar to a depth electrode which is currently used for epilepsy monitoring. This would take the form of a cylindrical probe which will be targeted to record and cool a specific sub-cortical structure such as the hippocampus or a part of the thalamus. Sensors and cooling elements will be placed along the length of this depth electrode like device. The cooling will be delivered at the tip of the probe or from the outer surface of the probe at regular intervals along the length of the device. Sensors will be interleaved between the cooling elements.

In accordance, and with reference to FIG. 2, each of the cooling sensing elements 66 has a layered configuration with a lowermost layer (that is the tissue contact layer) composed of the EEG electrode 34 centrally positioned on the cooling module 12. In addition to the elements discussed above, the cooling module 12 includes a cooling plate 70 positioned along the lowermost layer of the cooling sensing element 66 and to which the EEG electrode 34 is mounted. Secured to the backside of the cooling plate 70 is the thin-film thermoelectric cooling element 28 with a fast response time, high heat pumping capacity, and small/thin footprint.

On the side of the thin-film thermoelectric cooling element 28 opposite the cooling plate 70, a heat plate 72 and a heat spreader 30 are mounted. The heat spreader 30 can be composed of a phase change material, or may be a system containing a pumped fluid to convey heat away from the 'hot' side of the device. The components are mounted within a film supporting structure 42. In particular, the EEG electrode 34 and the components of the cooling module 12 are substantially integrated into the film supporting structure 42, while the temperature sensor 14 is mounted along the film supporting structure 42 at a position adjacent the cooling module 12 and the EEG electrode 34.

As discussed above, current practice for implantable devices for seizure control is built on experience gained from several decades of intracranial EEG monitoring for epilepsy surgery, but these practices have a number of built-in limitations, particularly the dependence on passive sensing and the lack of scalability of the number of intracranial EEG sensors. The present grid electrode system 10 brings powerful advanced engineering methodology to bear on sensing and intervention in epilepsy. The present grid electrode system 10 provides a cooling module 12 composed of a brain implantable, powerful thermoelectric element cooling 28 with a phase change material based heat spreader 30. The powerful, thin-film thermoelectric cooling element 28 used in accordance with the present invention is less than 600 micron thick.

It is appreciated the thermoelectric element cooling 28, as with any active cooling device, requires power for cooling. This input power in addition to the heat being pumped, is dissipated as heat from the "hot" side or reject side of the thermoelectric element cooling 28. This heat must be either removed from the system or stored. In accordance with the present invention, the thermoelectric cooling element 28 is combined with a heat spreader 30 composed of a heat absorber using a phase change material (PCM), a material which absorb heat quickly by undergoing a phase change and then slowly dissipate it. Among the various heat storage techniques, latent heat storage is particularly attractive due to its ability to provide a high storage density at nearly isothermal conditions. Phase-change thermal energy storage systems offer other advantages, such as small temperature difference between storage and retrieval cycles, small unit sizes and low weight per unit storage capacity.

As indicated above, heat must be dissipated from the "hot" side or reject side of the thermoelectric element cooling 28. This heat must be either removed from the system or stored. As a result of an epileptic seizure's relatively short duration and the need for a relatively fast cooling response to abate seizure activity, the thermoelectric element cooling 28 in combination with the heat spreader in the form of a phase change material based heat spreader 30 store short bursts of heat and dissipate the heat between seizures. A thermoelectric element cooling 28 with composite phase change material based heat spreader 30 is shown in FIG. 2. The phase change material has high thermal conductivity, high latent heat of fusion, biocompatibility (i.e., chemical inertness/stability such as paraffin), small volume change with no phase segregation, and low supercooling.

It is appreciated it is difficult to find a phase change material with all the desirable properties, especially high thermal conductivity (i.e., high heat exchange rate) and biocompatibility required for this application. This limitation on phase change materials is addressed by adding thermally conductive fillers to assist in heat transport throughout the volume of phase change material. The proportion of conductive filler to phase change material and the mechanical distribution of the two materials is optimized to ensure adequate heat flow rates without compromising heat storage capability. Examples of fillers include copper foam, carbon nanotubes and silver nanowires. Copper foam provides excellent isotropic conductive properties and can be machined. Carbon nanotubes, with their unique one-dimensional properties, have been widely researched as thermal conductivity fillers, although the thermal conductance at the interface dramatically degrades performance. Alternatively, Ag nanowires are 1-D nanostructured materials with the highest electrical and thermal conductivity (430 Wm-1K-1) of any metal and with good interface thermal conductance. Whether foam, nanotube or nanowire in combination with a phase change material matrix, the composite phase change material based heat spreader 30 employed in accordance with the present invention is integrated directly onto the surface of the thermoelectric element cooling 28.

Important factors in the design of the present thermoelectric cooling element 28 in combination with a phase change material based heat spreader 30 are the cooling rate, overall temperature change (switching speed), and power requirement (activation requirements). The cooling rate provided by a thermoelectric element cooling 28 depends on the response time of the thermoelectric element cooling 28 and the thermal resistance and capacitance of the object being cooled. Thermal capacitance of the brain is large, but only a fraction of it needs to be cooled. The introduction of a quick step function in temperature can be applied to maximize the thermal gradient across the depth of interest and minimize the time required to reach the critical temperature. As to the overall temperature change (switching speed), rapid response time, over-driving schemes and active control are employed to achieve the necessary temperature and time response. Drive power for a thermoelectric cooling element 28 is dependent on a number of variables, including the desired temperature differential (T) and the amount of heat that must be pumped (Q). Other factors that affect the chive power are the efficiency of the thermoelectric cooling element 28 itself, the thermal resistance behind the thermoelectric cooling element 28 and overdrive requirements.

As discussed above, brain cooling has been considered for a number of decades for application to head trauma, ischemia, cancer, pain and epilepsy. The present grid electrode system 10 integrates a responsive and addressable cooling function. To achieve local cooling, thin-film cooling elements are used, in particular, thin-film thermoelectric element coolers (TFTECs) 28, for their rapid response dine, high heat pumping capacity, and thinner and smaller footprint than current state-of-the-art coolers. The size and capability benefits make TFTECs 28 a desirable component for use in conjunction with the construction of a cooling and sensing array 32 in accordance with the present invention. The TFTEC 28 is integrated with opposed thermal plates and a unique composite phase change material based heat spreader 30 within a thin-film architecture 42.

As briefly mentioned above, the present grid electrode system 10 includes an integrated, modular, scalable, addressable thin-film cooling and sensing array 32. The present grid electrode system 10 integrates intracranial EEG electrodes 34 and temperature sensors 14, electrode leads, thin-film thermoelectric cooling elements 28, and phase change material based heat spreader 30 (that is, the cooling module 12) into an integrated, modular, addressable, scalable monolithic thin-film architecture 42. A monolithically integrated thin-film architecture 42 is utilized to minimize mass and volume and enhance device response and performance. The monolithically integrated thin-film architecture 42 allows scaling of the cooling and sensing array 32 in size and number of thin-film thermoelectric cooling elements 28, intracranial EEG electrodes 34 and temperature sensors 14.

As was also briefly mentioned above, the present grid electrode system 10 includes powerful and dependable functional electronics in the form of a control system 68 for active sensing, control of the thermoelectric cooling elements 28 and electrical stimulation of the EEG contacts. It is appreciated stimulation will be applied from the metal contact, that is, the EEG electrodes 34, but not from the contact area of the other types of sensors employed in accordance with the present invention.

The present grid electrode system 10 uses a fully implantable solution to condition and digitize signals intracranially, and close to the source, with a custom CMOS (complementary metal-oxide semiconductor) chip and transmit digital signals from that point on. This results in considerable improvement in signal fidelity as the length of leads will be reduced. This also aids scalability.

Temperature control is implemented to two distinct ways. The provision of two cooling modes provides greater flexibility in controlling the temperature of a focal part of the brain. In the first mode, called steady state mode, we will hold the temperature of a focal part of the brain is held at a lower temperature for several seconds or minutes. In the second mode, called pulse control mode, a focal part of the brain is rapidly cooled using one or snore brief pulses each of which will last for a few seconds to tens of seconds.

In order to provide for the number of cooling sensing elements 66 used in accordance with the present invention, the processing system as disclosed in U.S. patent application Ser. Nos. 12/184,664 and 13/429,109, which are incorporated herein by reference, will be implemented for use as a control system in accordance with the present grid electrode system 10. As will be appreciated based upon the following disclosure the processing (or control) system 110 can deliver a stimulation signal at different current strengths and be operated with wired, battery or RF (radio frequency) (13.56 MHz) power to condition, digitize and transmit digital signals over an infrared link to to/from a personal computer. It is, however, appreciated the power demands associated with the thermoelectric cooling elements will necessitate the utilization of an "on-board" power source. This power source and possibly data processing and storage unit may be contained, in a cavity in the chest of the user with power wires and possibly data wires extending between the device in the chest area and thin-film cooling and sensing array 32.

As will be appreciated based upon the following disclosure, the implantable wireless control system 68 employed in accordance with the present grid electrode system 10 measures brainwave signals, temperature characteristics and transmits them via an infrared signal through the skin/bone to an external infrared receiver for analysis. The implantable wireless control system 68 employed in accordance with the present grid electrode system 10 also provides the controlled application of power to the cooling sensing elements 66 for operation in accordance with the present invention. The implantable wireless control system 68 provides power using an external RF powered internally by a battery. The wireless control system 68 utilizes remote circuitry completely sealed within the body, usually in a cavity cut out in the skull.

When the implantable wireless control system 68 is powered by an external RF field, the implanted remote circuitry 74, and the cooling sensing elements 66 are electrically active only when external RF power is turned on and completely passive otherwise; it does not have any active electrical components when it is not being used. It is appreciated the cooling function in accordance with the present invention requires a large amount of energy requiring a rechargeable battery 29 (and/or super capacitors) implanted with such an embodiment of the grid electrode system 10. As will be appreciated, the system embodied in the '664 application and the 109 application disclose both a 4 channel system and a 64 channel. As is appreciated, the 64 channel offers a more robust processing system and will be described below, although it is fully appreciated those wishing to utilize a 4 channel system could similarly achieve the goals for the present invention. The implantable wireless control system 68 as disclosed with reference to FIGS. 3-8, permits the connection of the cooling and sensing array(s) 32 to remote circuitry and an external system through a reduced set of wires to transmit power and digital data. The embodiment of FIGS. 3-8 allows for the use of a small set of wires to transmit power to the remote circuitry 74 and the cooling sensing elements 66 of the cooling and sensing array and data from all cooling sensing elements in a single power and digital data stream.

The components of the control system 68 are multiplexer, amplifier, A/D ("analog to digital") converter, microprocessor, infrared transceiver, antenna, power supply, external receiver, and external power transmitter, all in communication with the cooling sensing elements described above. The cooling sensing elements 66 (including the EEG electrodes 34) forming part of the cooling and sensing array 32 are distributed over the brain surface and/or inserted into the brain. These cooling sensing elements 66 are connected to the remote circuitry 74, which as mentioned above is preferably mounted within a body cavity adjacent the cooling and sensing array 32. The internal remote circuitry 74 includes a multiplexer 180 that selects the appropriate cooling sensing element 66 to be measured and/or activated. The multiplexer 180 is controlled by the microprocessor 102e. The selected cooling sensing element 66 or "channel" is then amplified by an amplifier 120b which feeds the signal into an A/D converter 130. The A/D converter 130 is controlled by the microprocessor 120e which reads the data and sends it to an infrared transceiver which then sends an infrared signal through the skull, skin and/or tissue to an external receiver. The power supply picks up an external RF signal via the antenna, rectifies it and uses the rectified voltage to power the implant. The rectified voltage is regulated with a voltage regulator integrated circuit.

The remote circuitry 74 includes an RF inductive receive coil 114r and an infrared transceiver 116r for transmitting and receiving data with an infrared signal across the skin 18 of the patient being monitored. The IR ("infrared") transceiver 116r is aligned with a hole in the patient's skull in order to transmit and receive IR signals through skin 18.

The present wireless control system 68 also includes main circuitry 22. The main circuitry 22 includes an RF inductive transmit coil 14m to transmit power to remote circuitry 74 and an IR transceiver 16m to receive data from and send data to remote circuitry 74. Both inductive transmit coil 14m and transceiver 16m are located at the end of cabling 26 for the main circuitry 22 such that these elements can be conveniently positioned with respect to the head of the patient being monitored. RF inductive receive coil 114r within remote circuitry 74 receives power from an RE inductive transmit coil 14m which is part of main circuitry 22.

As mentioned above, and in contrast to the previously described embodiment, the wireless control system 68 includes a multiplexer 180 within the signal path of the remote circuitry 74. This change allows a single amplifier 120b and a single A/D converter 130 to be employed for multiple channels; allowing for scaling of the number of channels being recorded without an increase in space requirements, power consumption, and heat generation.

In accordance with a preferred embodiment, the wireless control system 68 samples each cooling sensing element 66 at a rate that is at least twice the highest frequency of the electrode signal. For example, if the desired bandwidth is 500 Hz then the sampling frequency is at least 1 KHz (Nyquist rate). Anti-aliasing filtering at the input of each channel, that is, cooling sensing element 66 connected, to the multiplexer 180 is achieved by the provision of an array of series L (as ferrite beads) and shunt capacitors 182 at the input of each channel on the multiplexer 180. In addition to limiting the frequency content of the input signal to be measured, the provision of an array of series L and shunt capacitors 182 at the input of each channel to the multiplexer 180 also filters out unwanted noise and the RE field powering the circuit.

The sampling duration is determined by the number of channels and the highest frequency of the signal. For example, and in accordance with an embodiment with 64 channels, if there are 64 channels and the highest frequency component of the signal is 500 Hz then the sampling rate would be 64 KHz and each channel would be sampled once every 1 msec for an interval of 15.6 µsec. It is important to measure each channel after the circuitry has had time to settle so there are no switching artifacts introduced into the measured signal.

The multiplexer 180 employed in accordance with a preferred embodiment of the present invention is effectively DC coupled. The circuit is AC coupled but the rapid switching of the multiplexer 180 and cooling sensing elements 66 makes it able to measure instantaneous DC voltages. The multiplexer 180 includes a low pass filter 184 at each channel input 186 and should be able to operate with an input potential of at least 100 millivolts above or below ground to accommodate the potentials measured within the human body. The DC power to the coupler is filtered with capacitors to reduce the noise from the other circuitry and the Rh field powering the remote circuitry 74. A resistor to ground is also provided at each channel input 186 to bleed off charge between measurement intervals.

The largest number of channels commercially available on a multiplexer is currently 32 channels. It is, therefore, appreciated the number of input channels can be increased by utilizing parallel multiplexers 180, 180b. Where parallel multiplexers 180, 180b are employed in accordance with the present invention, the address lines can be paralleled and the Enable pin 188, 188b is used to select specific multiplexers.

The rapid switching of the channel inputs 186 of the multiplexer 180 produces a high frequency signal at the output 190 of the multiplexer 180. That high frequency signal at the output 190 of the multiplexer 180 is modulated with the voltages of the cooling sensing elements 66 of the selected channels.

For example, and in accordance with a preferred embodiment employing 64 channels sampled at a 1 KHz per channel rate as discussed above, the output high frequency signal is a 15.6 (64 KHz) pulse that has 64 consecutive pulses modulated with the amplitude of each of the 64 channels, then it repeats over. The order or number of channels is set by the micro-controller 120e.

It is appreciated the multiplexer chosen for use in accordance with the present invention should have low channel resistance so the waveform can be acquired quickly with little attenuation and should also have low capacitance at the output so the circuit can respond to the rapidly changing channels.

As mentioned above, the present wireless control system 68 includes an amplifier 120b. In accordance with a preferred embodiment, the amplifier 120b is a high speed op amp that amplifies pulses modulated by the selected channels. The gain of the amplifier 120b is about 25 dB. The pulses for a 64 KHz system sampled at 1 KHz are 15.6 µsec in width. The amplifier 120b should have very low noise and respond with no overshoot or ringing. Ringing in the amplifier 120b can cause crosstalk into adjacent channels. A roll off capacitor is used in the feedback circuit to reduce the amplifier bandwidth for increased signal to noise ratio.

Only one amplifier 120b is needed for all the channels of the present wireless control system 68. The ability to amplify 64 channels of information with a single amplifier 120b achieves similar gain, offset and noise characteristics for all channels. Since the signals are high speed pulse signals, they are removed from low frequency noise such as Shot Noise and a small coupling capacitor can be used to couple the signal into the op amp.

The amplifier 120b is designed with additional circuitry capable of measuring DC voltages at the electrodes 112. The DC level is converted to pulse amplitude by the switching of the multiplexer 180.

The amplified signals are digitally converted by an A/D converter 130. The A/D converter 130 is a high speed 16 bit converter. The reference voltage for the A/D converter 130 is generated through a low noise reference voltage diode which serves to isolate the converted signal from power supply noise. The A/D converter 130 also has capacitors on the power supply to reduce noise. The A/D converter 130 is controlled by the micro-controller 120e. As with the prior embodiment, the micro-controller 120e is an 8-bit microcontroller.

The micro-controller 120e controls the A/D converter 130, the multiplexer(s) 180, 180b, the IR transceiver 116r and measures the power supply voltage. The micro-controller 120e receives commands and transmits data via the infrared transceiver 116r. The micro-controller 120e is programmable on the circuit board. The micro-controller 120e is also capable of receiving commands that instruct which channels to measure and to set the sampling rate. If a particular set of channels have signals of interest, it is possible it measure them with higher time resolution to increase waveform fidelity. It is also possible to ignore other channels if the signals are not useful or if the cooling sensing elements are damaged. In high noise environments, the micro-controller can measure and transmit channels multiple times to insure good data is received by the device outside of the body. By sensing the input voltage to voltage regulator the micro-controller can adjust the duty cycle, speed or data rate of the circuitry in proportion to the available power from the RF field. The micro-controller can also regulate the charging of the rechargeable battery taking into account the power used by the circuitry. In other words it can divide the power from the voltage regulator between the battery and circuitry depending on the available power and power requirements of the circuitry. This can greatly extend battery life and reduce the RF field needed to power the implant. In accordance with a preferred embodiment, the current used to charge the battery-would be scaled depending upon available power. The charge rate of the battery charger would be changed according to available power. This can be accomplished by the micro-controller setting an A/D voltage on the battery charger IC or by the micro-controller selecting a suitable charging resistor in the charging circuit.

Data and control communication is conducted over a standard IR data link. Each data frame transmitted by the implanted device, that is, the cooling and sensing array 32 and the remote circuitry 74, contains data for 64 channels, communication start and stop information and communication error detection information. When a frame is received by the main circuitry 22 a time-stamp is inserted into it. This time-stamp allows the intracranial data stream to be synchronized with a video data stream, thus allowing the data and video streams to be viewed in a synchronized manner if required.

The infrared transceiver 116r uses an infrared diode to transmit infrared signals through the body to an external infrared transceiver 16m or the main circuitry 22 and has an infrared photodiode to receive signals from an external transmitter. Since the Vishay infrared transceiver uses 2.2 volts and the supply voltage is 3.3 volts, another infrared diode is placed in the supply voltage for the transmitter part of the IR transceiver. This diode is then modulated along with the Vishay transmit diode. This increases the infrared signal power and increases the viewing angle at no additional cost in power. The infrared transceiver 116r is controlled by the micro-controller 120e and the data rate is adjustable.

Figure 3:
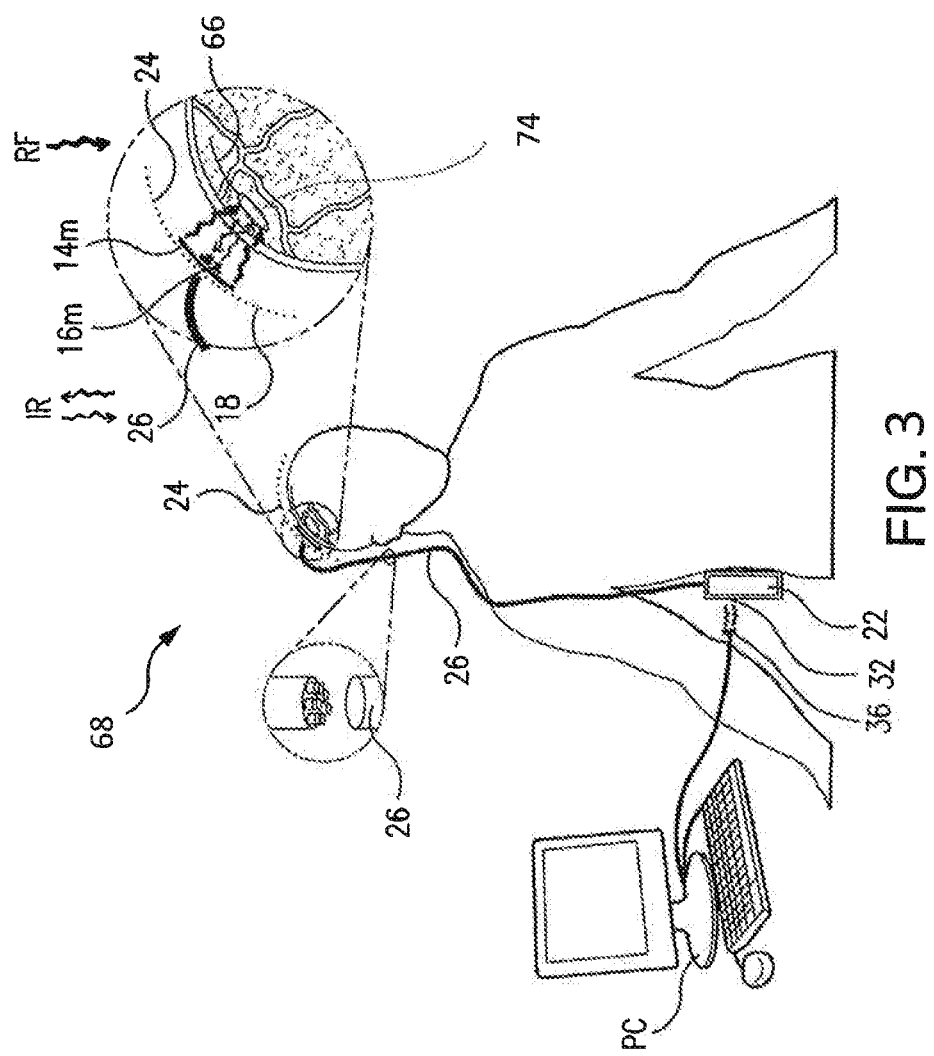
FIG. 3 is a schematic of the wireless control system employed in conjunction with the present grid electrode system.
Figure 4:
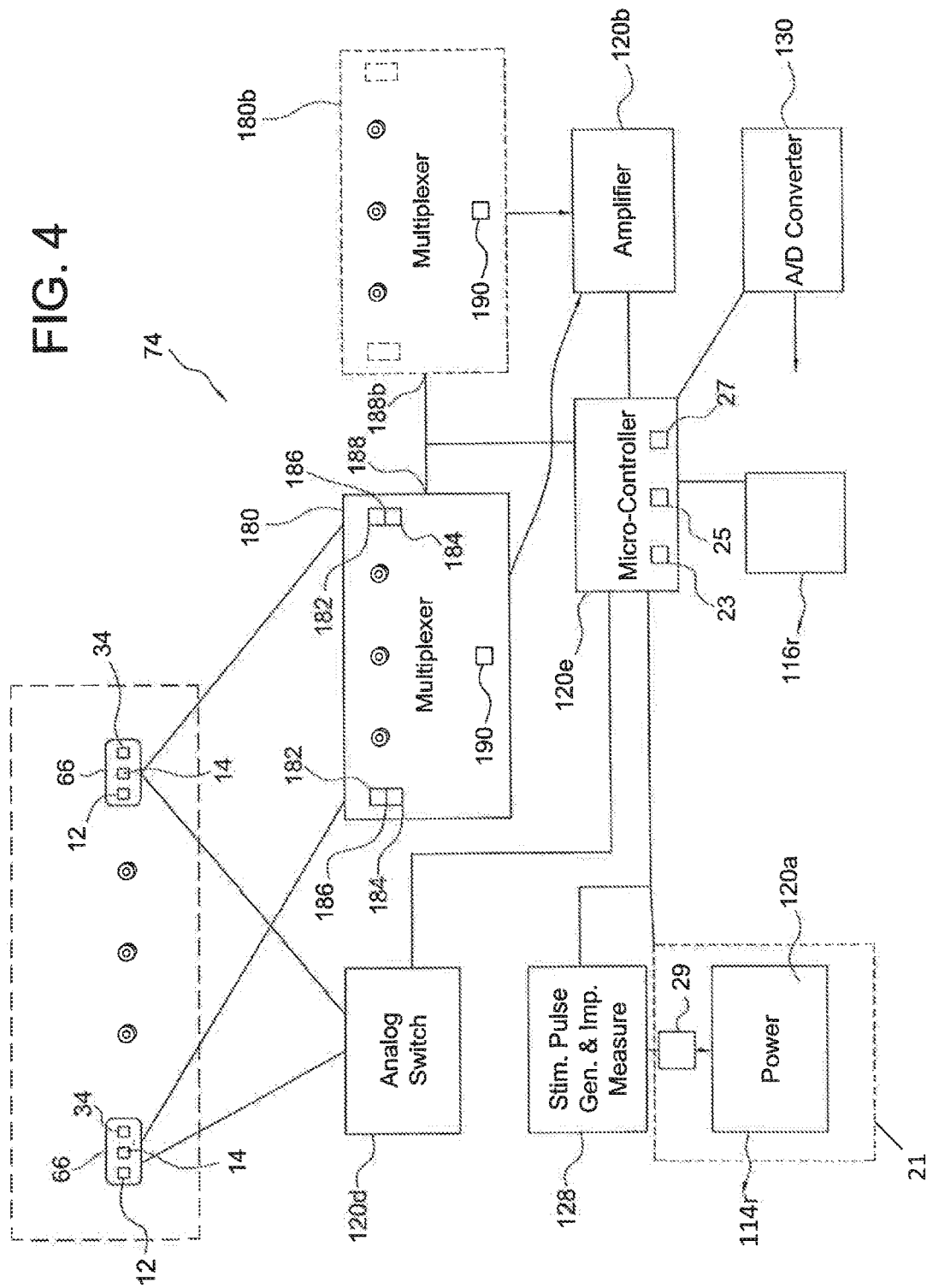
FIG. 4 is a functional block diagram of the remote circuitry and cooling and sensing array of the present grid electrode system.
Figure 5:
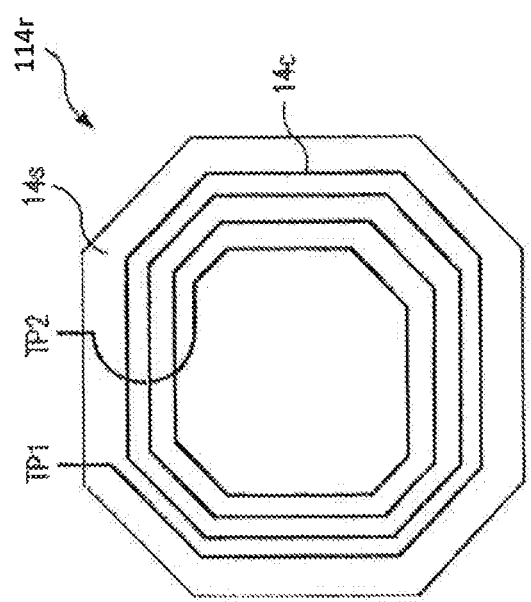
FIG. 5 is a schematic drawing of an RF inductive receive coil within the remote circuitry shown in FIGS. 3 and 4.
Figure 6:
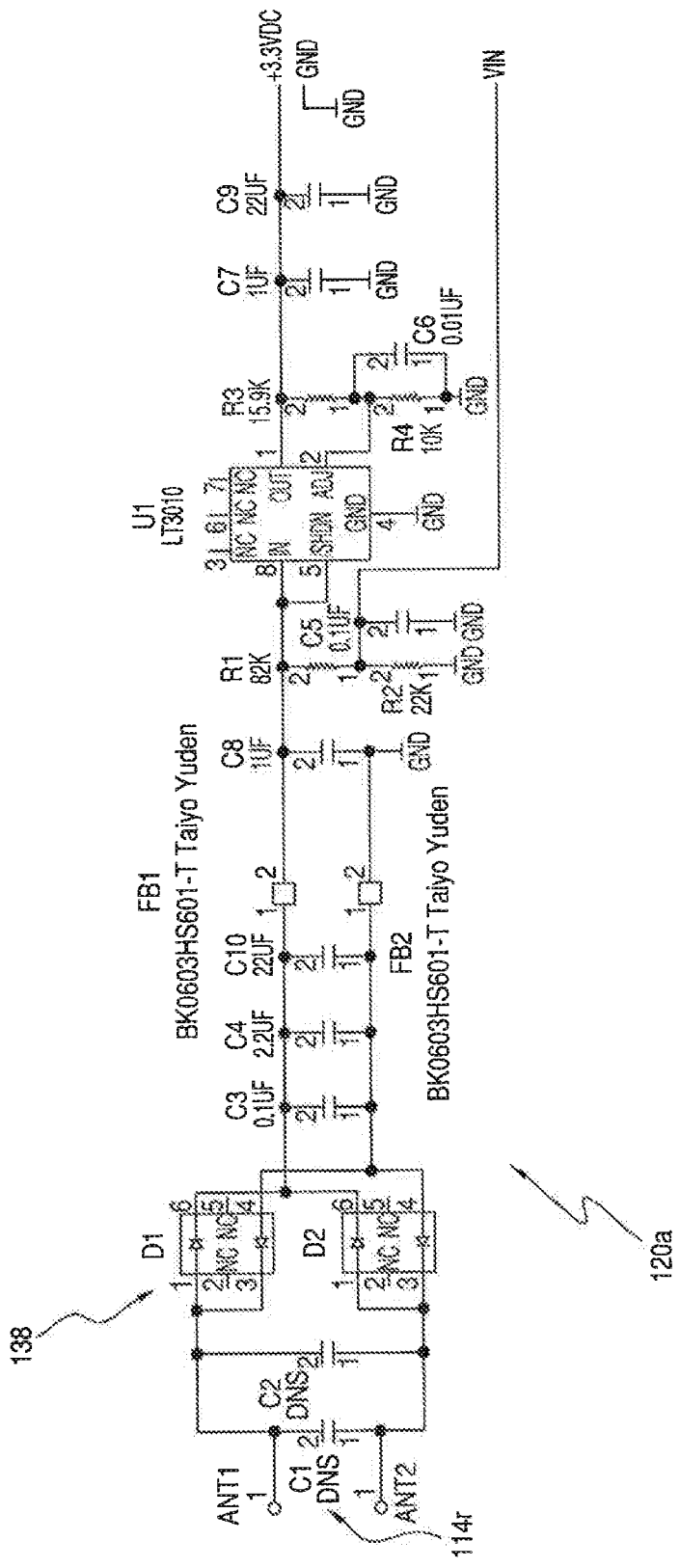
FIG. 6 is a circuit diagram of a portion of the remote circuitry illustrating an embodiment of the power circuitry therein. This embodiment of the remote circuitry is powered exclusively by power transmitted at RF frequencies.
Figure 7:
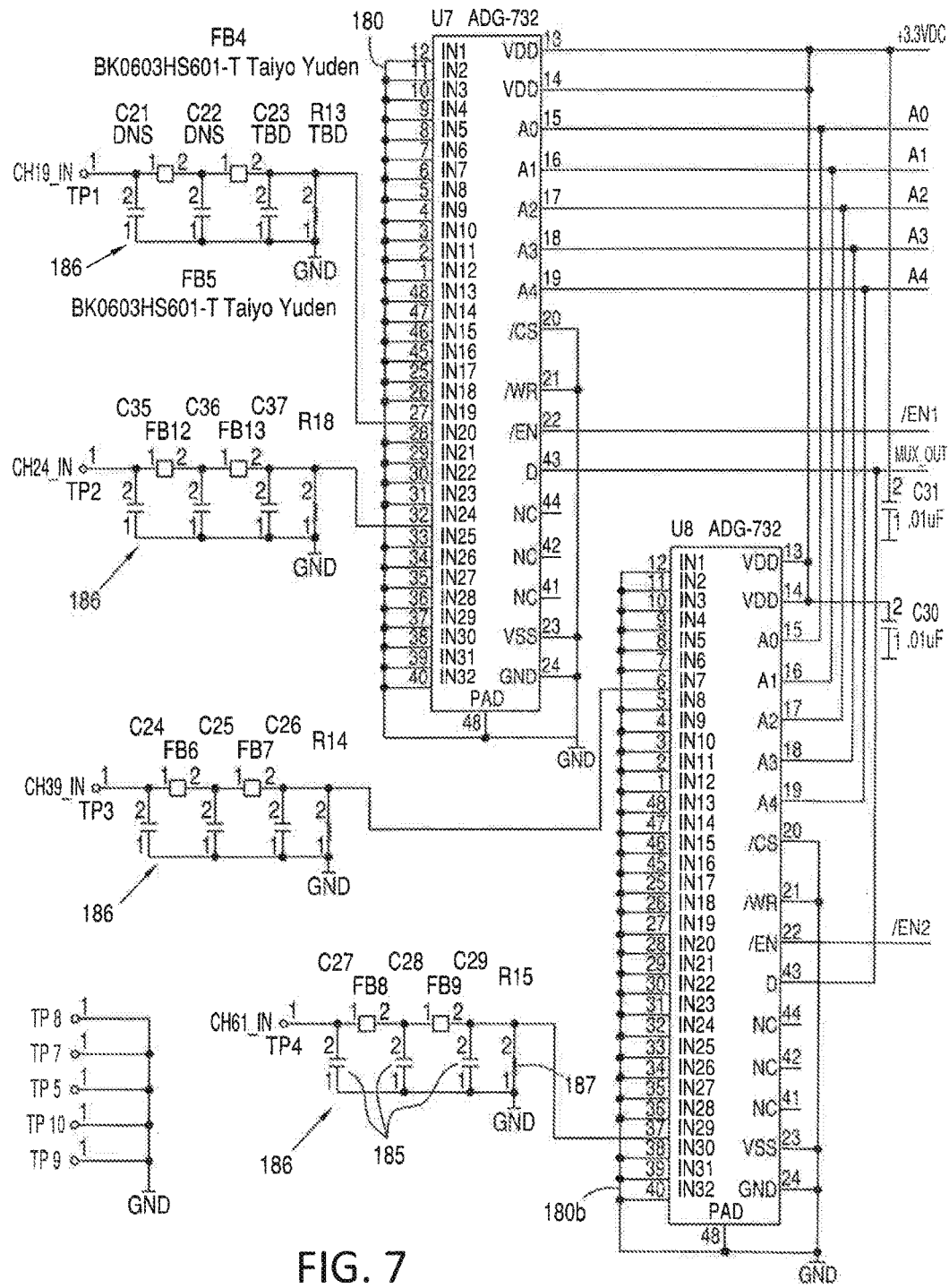
FIG. 7 is a circuit diagram of a portion of the remote circuitry illustrating an embodiment of the multiplexer therein.
Figure 8:
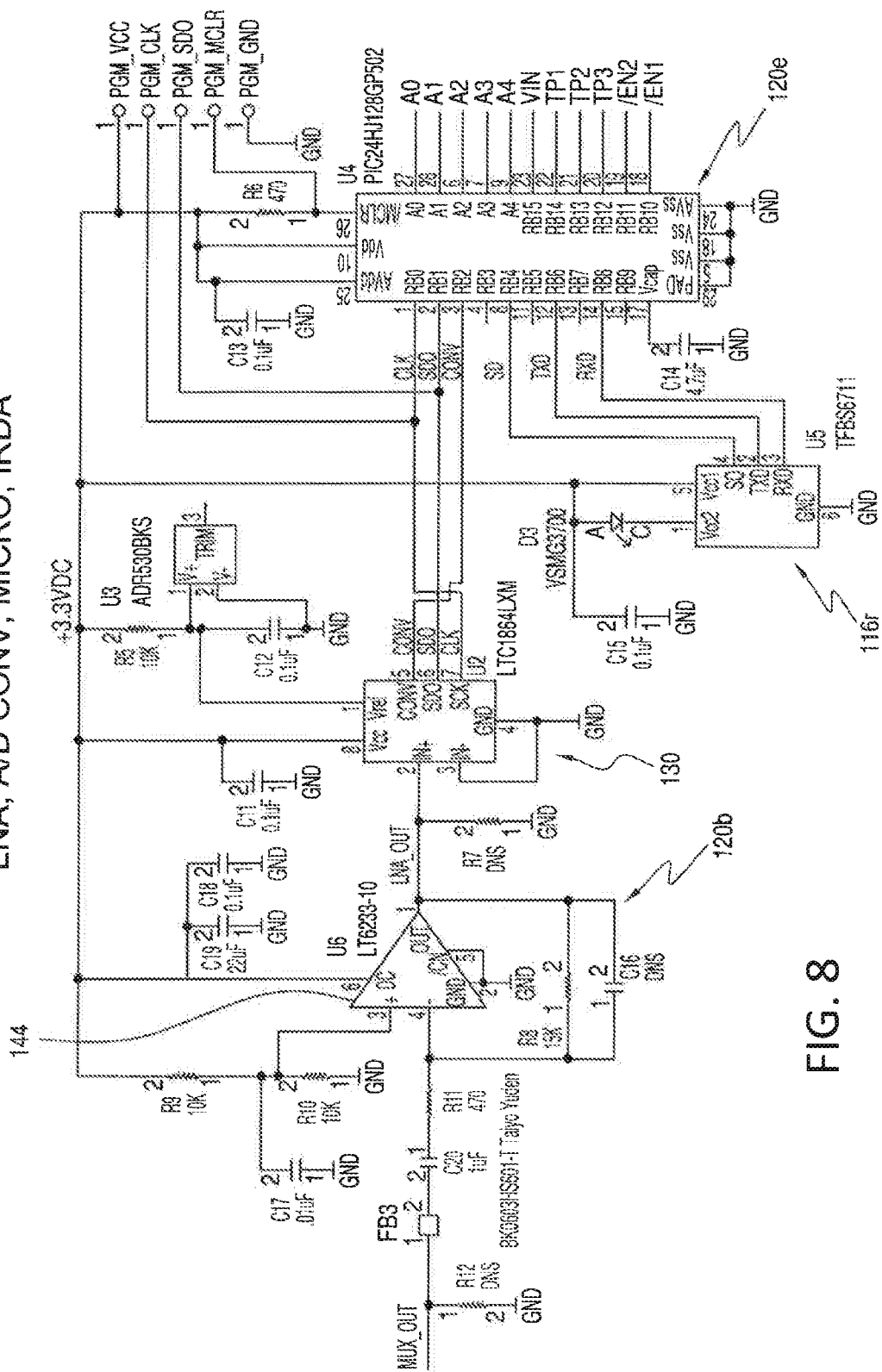
FIG. 8 is a circuit diagram of a portion of the remote circuitry illustrating an embodiment of the multiplexer therein.

With reference to FIGS. 6, 7, and 8 circuit diagrams of the embodiment illustrated and described generally in FIGS. 3, 4, and 5 are provided. Each of these figures shows a portion of remote circuitry 74 making up the present embodiment of control system 68. The portions of remote circuitry 74 are interconnected as labeled in the figures, according to standard practice within the field of circuit design, illustrating the various points at which the portions of remote circuitry 74 are joined.

In this embodiment, and as with the previously disclosed embodiment of control system 68, RF power is transmitted from main circuitry 22 to remote circuitry 74 preferably at a frequency of 13.56 MHz. This frequency is particularly well-suited to such an application since, as an FCC-designate ISM ("industrial, scientific and medical) band set aside for industrial, scientific and medical devices, the band of 13.553 to 13.567 MHz (centered on 13.560 MHz) is the ISM band which has the lowest loss and least heating of body tissue. (See the Handbook of Biological Effects of Electromagnetic Fields by Polk and Postow, CRC Press, p. 88-91, 1991.) Biological tissue at 13.56 MHz has the lowest conductivity which means that the RF signal will penetrate the tissue to the greatest depth at this frequency.

At a frequency of 13.56 MHz, inductive receive and transmit coils such as 114r and 14m primarily create a magnetic field confuted to the locality around the coil. The field diminishes rapidly with distance from the coil, much more rapidly than an electric field under the same circumstances. Thus, the fields which couple the coils are the near fields of the coil. The near field contains the propagating field, the energy storing both the electric and magnetic fields. In the near field, there is much more energy per unit volume available than in the far field; therefore, a higher degree of coupling can be achieved than in the far field alone, thereby increasing the energy transfer efficiency of the circuits.

FIG. 6 is a circuit diagram illustrating an embodiment of voltage regulator (or power) circuitry 120a within remote circuitry 74. RF inductive receive coil 114r receives power from main circuitry 22 through RF inductive transmit coil 14m, and this power is rectified and conditioned in voltage regulator circuitry 1210 of remote circuitry 74 for storage in the battery 129 and use in accordance with the present invention. Four Schottky diodes 138 (also labeled in pairs as D1 and D2) are configured as a full-wave rectifier to condition the power. The diodes may be Schottky barrier diodes such as diode RSX051VA-30 available from Rohm Co., Ltd. of Kyoto, Japan. The configuration of all of the components integrated into the remaining circuitry of FIG. 6 is standard and well-known to those skilled in the art of circuit design to provide clean and regulated DC power.

FIG. 5 is a schematic drawing of an RF inductive receive coil within the remote circuitry of control system 68 of FIGS. 3 and 4. As shown, RF inductive receive coil 114r is a flexible printed circuit coil consisting of metallic conductors 114c deposited onto substrate material 114s such as Mylar film. Coil 114r is connected to voltage regulator circuitry 120a at points ANT1 and ANT2 as shown in FIG. 6. Coil 114r is not limited to the configuration as shown in FIG. 5. For example, coil could be coiled magnet wire in a number of other coil forms. FIG. 5 is also an illustration of inductive transmit coil 14m since one embodiment of coil 14m may be essentially identical to coil 14r.

FIG. 7 illustrates a preferred embodiment of the dual multiplexer 180, 180b arrangement described above. In accordance with a preferred embodiment, the multiplexers 180, 180b are ADG-732 monolithic CMOS 32 channel/dual 16 channel analog multiplexers available from Analog Devices of Norwood, Mass. Representative channel inputs 186 are disclosed. Each channel input 186 includes a low pass filter 184. In addition, the DC power to the coupler is filtered with capacitors 185 to reduce the noise from the other circuitry and the RF field powering the remote circuitry 74. A resistor 187 to ground is also provided at each channel input 186 to bleed off charge between measurement intervals. The configuration of the components integrated into the remaining circuitry of FIG. 7 is standard and well-known to those skilled in the art of circuit design to provide for the multiplexing of the channel signals received from the various electrodes 112.

In particular, the multiplexers 180, 180b take a low frequency signal (that is, the signals from the cooling sensing elements 66) and "chop" it at a high rate to make it a 64 KHz signal. The resulting signal appears as a narrow pulse (15 μsec) every 1 msec. This is combined with 63 other channels to give 64 consecutive pulses of 15 μsec each. The amplitude of each pulse is the instantaneous amplitude of the sampled low frequency signal on each of the 64 channels. The high frequency amplifier 120b sees a signal of 64 KHz and amplifies it. The signal is actually a sampled composite (1 KHz sample rate) of the 64 channels of low frequency signal. 1 KHz is the Nyquist sampling rate for a low frequency signal containing components to 500 Hz. As explained herein in greater detail, the output of the amplifier 120b is then A/D converted by the A/D converter 130, and sent to the computer (PC) via infrared where it is synchronously detected and reassembled back in to 64 channels of low frequency signals.

FIG. 8 illustrates the micro-controller 120e, amplifier 120b, infrared transceiver 116r and A/D converter 130 of the remote circuitry 74. As noted the output of the multiplexer 180, 180b is input to the amplifier 120b which is preferably configured using an operational amplifier 144 in a standard instrument amplifier configuration within accompanying resistors and capacitors as shown in FIG. 7. Such configurations are well-known to those skilled in the art of circuit design. Operational amplifier 144 may be a model LT6233-10 integrated circuit operational amplifier chip available from Linear Technologies Corporation of Milpitas, Calif. The output of operational amplifier 144 is communicated with the A/D converter 130 which is ultimately linked to the micro-controller 120e and the infrared transceiver 116r in a conventional manner. Such configurations are well-known to those skilled in the art of circuit design. In accordance with a preferred embodiment, the A/D converter may be an LTC1864 16-bit A/D converter available from Linear Technologies Corporation of Milpitas, Calif., the micro-controller may be a PIC24HJ128GP502 micro-controller available from Microchip Technologies Inc. of Chandler, Ariz., and the infrared transceiver may be a TFBS6711 low profile infrared transceiver available from Vishay Electronic GmbH, Selb, Germany.

With reference to FIG. 5, and as briefly discussed above, the antenna, that is, the coil inductive receive coil 114r of the remote circuitry 74, is used to receive a 13.56 MHz magnetic field signal which is rectified and applied to a voltage regulator. The antenna output is a balanced output with both signal legs rectified and filtered. One of the filtered outputs is applied to ground, the other to the voltage regulator. The filtering of the dual legs is to keep the 13.56 MHz signal from entering in to the circuitry. The antenna is a coil that is parallel tuned with capacitors to 13.56 MHz. The coil can take the form of wires, printed traces and have a center slug of permeable material to increase the magnetic field passing through the coil. The slug would reduce the amount of external R/F field to achieve a given power level in the implant. The antenna can range in size from about 2.5 sq. in. (16.13 sq. cm) down to less than 0.25 sq. in, (1.61 sq. cm). The small antenna would be used in cases such as when the RF transmit antenna is collocated over the implant antenna. The larger antenna would be used when the device is deployed in freely moving animals. Antennas in close proximity have stronger coupling and less loss.

The power supply is a straight low noise linear low drop out regulator. A linear regulator has much less noise than a switching regulator. For a 3.3 volt output the linear regulator requires a voltage of at least 3.5 volts on the input. The regulator can regulate with input voltages in excess of 20 volts.

The cooling sensing elements 66 are connected by an analog switch network 120d. The analog switch network 120d creates connections between individual electrodes and functional circuitry 128 which provides tissue stimulation current and which enables remote circuitry 74 to measure impedance under the control of the micro-controller 120e.

The IR transceiver 16m of the main circuitry 22 is an infrared transmitter and receiver. It can be as simple as a standard IrDA ("Infrared Data Association") dongle that plugs into the USB ("universal serial bus") port of a computer. It operates on standard IrDA formats. It communicates bidirectionally with the IR transceiver 116r in the remote circuitry 74. If necessary the viewing angle of the infrared link can be increased by placing it in an environment that has reflective surfaces iii the infrared region.

The external RF transmitter 14m is a 13.56 MHz CW (continuous wave) transmitter. The signal is received by the antenna 114r and rectified to power the implant. The transmitter 14m uses a transmit coil to generate the RF field. The coil can be large (1 sq. ft. (929 sq. cm to power the implant in a freely moving animal or very small (<0.25 sq. in. (<1.61 sq. cm)) when used in humans and collocated with the implant antenna. Less RF power is needed if the implant and external antenna are close together. The coupling between the antennas is optimized when they are of the same dimensions and shape. The Rh transmitter power can range from 250 mW to over 5 watts depending on the coupling distance and orientation between the antennas. The RF transmitter power can be adjusted to adjust the voltage input to the power supply in the implant. The micro-controller measures the supply input voltage and sends this data out through the IR transceiver 116r. This information can be used to adjust the output power of the external Rh transmitter 14m.

It is appreciated although the control system 68 described above facilitates scaling for the cooling sensing elements, a considerable limitation of current methodology is the lack of real time measurement of modalities other than electrical activity, for example pH, ionic currents, and neurotransmitters. As such, the present grid electrode system 10 employs a cooling sensing element 66 for concurrent, real-time, in situ measurement of both field potentials and localized neurochemistry (example, potassium and pH). The cooling sensing element could be a FET ("field-effect transistor") based device such that a sensed signal is immediately amplified by the sensor. The sensors for these modalities are co-localized and interface directly with conventional data collection equipment and the wireless system. The cooling and sensing array 32 can measure pH, and sensors for K+ and temperature are currently being incorporated.

Coordinated operation of the various components making up the present system will be achieved via the implementation of a seizure detection algorithm based on Teager energy, a non-linear weighting of the signal such that higher-frequency content is emphasized relative to low-frequency content and seizure prediction approaches using connectivity measures. This approach can be used to detect seizures and discriminate seizure from background activity accurately and efficiently. An earlier version of the seizure detection algorithm has been reported (Zaveri H P, Williams W J and Sackellares J C (1993). Energy based detection of seizures. Proceedings of the Annual International Conference of the IEEE Engineering in Medicine and Biology Society, USA, IEEE). A multiple-input and multiple-output (MIME)) control algorithm will be used to control thermoelectric cooling element 28 temperature based on detected signals, and sensed temperature (Goodwin G, Graebe S and Salgado M (2001). Control System Design, Prentice Hall). The control algorithm will be used to select one or more sets of cooling elements to activate. Among the elements in a set, one will be designated as the focus (primary) cooling element while neighboring elements will be secondary. The control algorithm will cool the focus element to a greater amount than secondary elements. These algorithms will be implemented on the microcontroller which will be embedded with the implanted electronics.

In accordance with a embodiment of the present invention, and with reference to FIGS. 9(a) and 9(b) where similar reference numerals are used for elements similar to those described above, the intracranial EEG preamplifiers, stimulation, and cooler control of the remote circuitry 74 is achieved using CMOS chip(s). FIG. 9(a) shows a physical illustration of a cooling and sensing array 32 composed of cooling sensing elements 66 having 3×3 (Aim 3) and 8×8 (Aim 4) intracranial EEG electrodes or contacts 34, temperature sensor 14 and cooling module 12 as described above. The cooling sensing elements 66 are linked to the remote circuitry 74 which is in the form of a CMOS chip incorporating signal processing circuitry and the wireless infrared transceiver 116r. An exemplary CMOS chip implemented in the remote circuitry 74 is shown in FIG. 9(b). As seen in the figure, after being selected based upon the stimulation selector 150 for each cooling sensing element 66, the intracranial EEG present at each cooling sensing element 66 is amplified by a low-noise, low-power, differential AC preamplifier 152 with proposed gain equal to 100 V/V and input-referred noise of less than 2.2 µVRMS at minimum power consumption. The preamplifier preferably will contain series input capacitors and capacitive feedback in parallel with high-value MOS transistor resistances. The series input capacitors will block neural DC offsets in the intracranial signals, while the feedback capacitors will provide precise control of the voltage gain as suggested in Harrison RR and Charles C. A Low-Power Low-Noise CMOS Amplifier for Neural recording Applications, IEEE journal of Solid-State Circuits 2003; 38: 958-965. The anticipated range of operation is from less than 1 Ha to approximately 5 kHz (Kmon P. Low-Power Low-Noise Versatile Amplifier for Neural Signal. Recording. International Conference on Signals and Electronic Systems (IC-SES 2008), Kraków, Poland 2008: 141-146.). To conserve power, selected preamplifiers may be powered off when not needed.

The CMOS chip will enable rapid switching of each bidirectional neural contact connection between its preamplifier input and programmable-level, biphasic, square-wave stimulation current at 50 Hz with 200 µs pulse width for function mapping and user selectable frequency (from a pre-defined range) for therapy. Due to charge injection, each stimulation event causes the intracranial EEG signal to be unreadable for a period of time. This is called the "stimulation artifact" and can last hundreds of milliseconds (Blum R A, Ross J D, Brown E A and DeWeerth S P. An Integrated System for Simultaneous, Multichannel Neuronal Stimulation and Recording. IEEE Transactions on Circuits and Systems—I 2007; 54 (12): pp. 2608-2618). This duration can be reduced to less than 2 ms using active feedback (Blum R A, Ross J D, Brown E A and DeWeerth S P. An Integrated System for Simultaneous, Multichannel Neuronal Stimulation and Recording. IEEE Transactions on Circuits and Systems—I 2007; 54 (12): pp. 2608-2618) or to 450 µs using a switched capacitor solution (Gusmeroli R, Bonfanti A, Borghi T, Spinelli A S and Baranauskas G. A switched-capacitor neural preamplifier with an adjustable pass-band for fast recovery following stimulation. Conference Proceedings: Annual International Conference of the IEEE Engineering in Medicine & Biology Society 2006; 1: 652-5). While the currently proposed stimulation method involves preset current levels, future iterations will potentially include mote advanced proportional feedback methods, such as those proposed in Colpan M E, Li Y, Dwyer J and Mogul D J. Proportional feedback stimulation for seizure control in rats. Epilepsia 2007; 48 (8): 1594-603.

As discussed above, each cooling sensing element 66 has an associated EEG electrode 34, cooling module 12 and temperature sensor 14, The temperature sensor output will be conditioned and routed alongside the amplified intracranial EEG signal to the multiplexer 180. The temperature information is used to control the associated cooling module via a reverse path toward the cooling sensing element 66. Digital control data within the chip control preamplifier enabling, stimulation control, multiplexer selection, and cooler control.

The amplified intracranial EEG signals will be sequentially transmitted through the multiplexer 180 to an analog to digital (A/D) converter 120b having the resolution and sample rate described above. To improve the reliability of the implanted system, we will incorporate a simple fault-tolerant strategy based on hardware redundancy (Lanning B, Joshi B, Kyriakides T, Spencer D and Zaveri H (2011). Emerging technologies for brain implantable devices, Epilepsy: The intersection of Neurosciences, Biology, Mathematics, Engineering and Physics, In press. I. Osorio, H. Zaveri, M. Frei and S. Arthurs, CRC Press). For example, it is contemplated to use one spare intracranial EEG contact and preamplifier for every 2×2 sub-array of sensors. This will ensure that a failed contact can be replaced by a spare contact in close proximity to it. Additionally, we will use multiple reference electrode contacts and a redundant A/D converter 120b' to further improve system reliability. An initial reliability analysis suggests that this approach will add an adequate level of reliability to the system. Other fault-tolerant strategies will also be evaluated. The remote circuitry 74 will further include a controller 75 and a processor for digital EEG and temperature data 77, as well as an infrared transceiver 116r.

As briefly mentioned above, it is appreciated larger cooling and sensing array 32 for human use are desired. The geometry of thin-film heat spreaders for such and application are optimized for lateral cooling uniformity and co-location of resistance temperature sensors and intracranial EEG electrodes. The cooling and sensing array will also be evaluated in combination with the control system to test operation and performance of the entire system.

It is expected the present grid electrode system 10 offers a significant achievement for three reasons. First, by developing such a system relating to the use and understanding of local brain cooling, an alternative and complimentary methodology for controlling the expression of seizures that can be better directed and better controlled than electrical stimulation. Electrical stimulation as a therapeutic option for seizure control has received considerable attention in the past decade. Three first generation devices, from Cyberonics, Medtronic, and NeuroPace are in use or in clinical trials. Two of them (Cyberonics and Medtronic) are chest implanted open-loop systems that periodically stimulate a part of the brain or a nerve leading to the brain, with the latter approach having been used in more than 45,000 patients for the treatment of epilepsy or depression. The third is a brain implantable responsive device which stimulates selected brain areas. Intervention results because electrical stimuli interrupt function between two electrode contacts or in the case of the NeuroPace device also between the electrode contacts and the device body. The assumption is that electrical stimuli emitted from one electrode contact travel to a second electrode contact in a cathode-anode pair. The formation of a cathode anode pair, however, is doubtful in a medium which offers multiple alternate current paths to electrical charge. In our test, in humans, of a prediction of a computational study performed by the Hopkins group (Nathan S S, Sinha S R, Gordon B, Lesser R P and Thakor N V. Determination of current density distributions generated by electrical stimulation of the human cerebral cortex. Electroencephalography & Neurophysiology 1993; 86 (3): 183-92), we confirmed that when excitatory stimuli are delivered to intracranial EEG electrode contacts separated by more than 2 cm they do not form a cathode-anode pair, activating tissue between stimulated contacts, but rather result in activation of tissue around a stimulating electrode contact (Gwinn R P, Spencer D D, Tkeshelashvili Duckrow R B, Vives K P, Spencer S S and Zaveri H P. Changes in local cortical ECoG activity with 50 Hz stimulation in humans. Epilepsia 2008; 49 (9) 1602-1610).

Second, the device will allow improved mapping of brain function and the ability to perform reversible functional ablation in the epilepsy monitoring unit (EMU). Of the approximately 2.1 million patients with epilepsy in the USA, about 600,000 could be appropriate candidates for surgical resection. Almost half, however, require intracranial EEG monitoring to localize an epileptogenic source for their seizures. Almost half of those patients either are not candidates for resection or fail surgical control. The most common reasons we are unable to carry out successful surgery are either the identification of multiple foci or, most commonly, the overlap of non-dispensable function with the epileptogenic region. In some instances, surgeons will hesitate to resect association cortex such as parietal or frontal locations because one cannot readily predict the cognitive or behavioral consequences of a given resection volume. This often results in leaving behind epileptogenic tissue and failure of seizure control.

Intracranial electrodes are used to inactivate tissue between a pair of contacts to map function in the EMU. Local cooling has the potential of providing a more accurate functional localization not only because it can inactivate a more restricted region of cortex with no discernible effect on normal cortical function (Rothman S M and Yang X.-F. Local Cooling: A Therapy for Intractable Neocortical Epilepsy. Epilepsy Currents 2003; 3 (5): 153-156; Tanaka N, Fujii M, Imoto H, Uchiyama J, Nakano K, Nomura S, Fujisawa Kunitsugu I, Saito T and Suzuki M. Effective suppression of hippocampal seizures in rats by direct hippocampal cooling with a Peltier chip. Journal of Neurosurgery 2008; 108 (4): 791-7), but also because non-contiguous areas and areas with greater spatial complexity than that between a pair of electrode contacts can be mapped. We note, for example, that an area underlying 3 electrode contacts cannot be simultaneously inactivated by electrical stimulation because of the limitation to pairwise activation. Local cooling also removes the possibility of stimulation-induced seizures that confound the interpretation and lengthen the duration of mapping procedures. A cooling and sensing array 32, with its unique ability to interrupt function over complex spatial areas will also allow the surgeon to perform reversible functional ablation in the EMU which can considerably help in the planning of respective epilepsy surgery, particularly when the areas to be resected lie close to sensitive function which must be protected. A cooling and sensing array 32 may provide a solution both for seizures emanating from functional tissue and to perform a reversible functional ablation of a much larger volume of brain than present point to point electrical stimulation can provide. For example, patients with suspected occipital lobe epilepsy could have grids placed over the occipital region in order to verify the volume of occipital lobe involved in generating the seizure. After capturing several seizures in the EMU, the seizure onset area could be reversibly cooled demonstrating the extent of visual field cut and the patient's tolerance of that neurological loss. The same scenario would apply for non-dominant visual spatial function in parietal lobe epilepsy or testing of attention and organization in areas of frontal lobe in a respective field. Certainly, cooling might provide for a much cleaner, more tightly defined comprehensive language region in the dominant parietal temporal epilepsies, Second, in many instances the temporary cooling along with the epilepsy field localization demonstrates such overlap that resection is impossible, and under these circumstances responsive cooling of the region may halt seizure spread without permanent neurological injury. That is, the cooling sensing array may be left in place and used instead to control seizures instead of proceeding to surgery for epilepsy.

Finally, a cooling and sensing array 32 is an augmented sensing device, which when implanted in an epilepsy patient for the control of seizures will also monitor and document theft seizure activity. This long-term documentation outside the EMU, without the effect of AED ("antiepileptic drugs") taper and surgery to place electrodes (Spencer S S, Goncharova I I, Duckrow R B, Novotny E J and Zaveri H P. Interictal spikes on intracranial recording—behavior, physiology and implications. Epilepsia 2008; 49 (11): 1881-1892; Zaveri H P, Pincus S M, Goncharova I I, Duckrow R B, Spencer D D and Spencer S S. Localization-related epilepsy exhibits significant connectivity away from the seizure-onset area. NeuroReport 2009; 20 (9): 891-895; Zaveri H P, Pincus S M, Goncharova I I, Novotny E J, Duckrow R B, Spencer D D and Spencer S S. A reduction in energy accompanies anti-epileptic drug taper during intracranial monitoring, Epilepsy Research 2009; 86 (2-3): 153-62; Zaveri H P, Pincus S M, Goncharova I I, Novotny E J, Duckrow R B, Spencer D D and Spencer S S. Background EEG spectral change with anti-epileptic drug taper during intracranial monitoring. Clinical Neurophysiology 2010; 121 (3): 311-7), is expected to improve the localization of areas involved in seizure onset.

It is appreciated that the disclosed device is highly complex and offers a variety of potential uses and implementations. As described above, a fully implantable cooling and sensing array with fault tolerance is disclosed. As explained above, the device includes a PCM based back-end, wireless power, which is possibly battery backed, and implanted electronics to sense, amplify, filter and digitize sensor signals, and control cooling functionality and seizures. The device also includes fault tolerance, initially for the sensing functionality (redundant sensor contacts, redundant reference electrodes), and later for cooling modules.

As discussed above, the device is appreciated to provide three possible uses: (1) map brain function, (2) reversible functional ablation to test the effect of a surgery, and (3) control seizures. The first two functions will be performed in the ward (that is, in the epilepsy monitoring unit or EMU). The third function will be performed in a fully implantable manner.

With this in mind, the present device may take various forms, combining necessary features as required for implementation of specific functionalities. For example, it may be implemented as a cooling and sensing array with fluid based back-end. Such a device will be used for mapping brain function and reversible functional ablation. The device will be used while the patient is in the ward. The electronics will be used to control the cooling function of the device and will be housed external to the body. The power source will be external to the body, and power will be delivered in a wired manner. The fluid to cool the back end will be pumped in/out of the device from outside the body.

The device could also be implemented as a cooling and sensing array with PCM based back-end. Such an implementation would be similar to the cooling and sensing array with a fluid based back-end, but will have a back-end containing a PCM or other heat absorber. The electronics and power will remain external to the body.

Further it might be implemented as an implantable cooling and sensing array. This device will have a PCM based back-end, wireless power, which is possibly battery backed, and implanted electronics to sense, amplify, filter and digitize sensor signals, and control cooling functionality and seizures.

The present brain cooling system is designed to be safe and effective. This is achieved by ensuring that the system is composable, certifiable, interoperable, dependable, and fits well with the operating environment. This system is developed based on the idea of a cyber-physical-environment ("CPE") or CPE continuum where the system is logically composed of three subsystems: cyber, physical and environment (brain). The physical subsystem is composed of the cooling device, associated sensors, electrodes, power, and the communication and hardware infrastructure. The cyber subsystem consists of data, seizure detection, and all the control strategies, including controlling the cooling device to control seizures.

Composability has ensured the ability to predictably compose subsystems out of modules and the brain cooling system out of subsystems. In general, composability encompasses ways to assure composition of dependable subsystems from modules, systems from subsystems, and a network from systems with an ability to do so predictably.

Recognizing that the existing regulatory evaluation of medical devices involves extensive testing leading to high costs and long lead times from conceptualization to commercial availability, and that this process will be much more involved and expensive for more complex systems, such as the brain cooling system, the present invention places a special onus on certifiability. Accordingly, the system is divided into subsystems and modules for a hierarchical certification process so that certification of modules could be used for the certification of the composed subsystem and that certifications of the subsystems can be used for the certification of the complete brain cooling system.

Usually medical devices are designed to operate as standalone units working in isolation. Although these devices may have the capability to stream data to electronic health records and the potential to integrate with various disparate medical devices to function as a single system, such integration is currently often not allowed due to safety concerns. The goal of interoperability is to enable a seamless flow of information between many disparate devices over a network. Such interoperable devices offer clear advantages to both the patient and the care provider, such as better assessment of the patient's health through fusion of information from the various devices. Expecting that the brain cooling system could be used in conjunction with other medical devices, the present invention addresses the issue of interoperability.

Furthermore, the system is able to accommodate different levels of users, such as the patient, nurse, and physician and it operates seamlessly with other medical monitoring and data acquisition and analysis systems. The support for different levels of users offers protection against unauthorized access to the device.

The system is safe from the dependability point of view. Although the system is manufactured from high quality components, it can still be susceptible to failure due to ageing and the operating conditions. The system dependability is improved by incorporating fault-tolerant techniques. One of these techniques is similar to what is proposed in (Acahrya et al., 2011). [Acharya-2011] Acharya I, Joshi B, Lanning B, and Zaveri H, "Reconfigurable Fault-Tolerant Multielectrode Array for Dependable Monitoring of the Human Brain" Proceedings of 33rd IEEE EMBS'11 conference, Boston, Mass. (June 2011).

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A clinical grid electrode system for seizure control through local cooling, mapping brain function and the provision of reversible functional ablation comprising:
   a modular, addressable, scalable, cooling and sensing array composed of a plurality of cooling sensing elements, wherein each of the cooling sensing elements is composed of a cooling module, a temperature sensor and an EEG electrode mounted within a film supporting structure; and
   a control system to which the cooling and sensing array is coupled for providing for control and monitoring of the cooling sensing elements making up the cooling and sensing array.

2. The clinical grid electrode system according to claim 1, wherein the cooling module includes an active thermoelectric cooling element with a fast response time, high heat pumping capacity, and small/thin footprint.

3. The clinical grid electrode system according to claim 2, wherein the cooling module also includes a phase change material based heat spreader.

4. The clinical grid electrode system according to claim 1, wherein the control system includes electronics for power, thermoelectric element driving, temperature sensing, and signal conditioning.

5. The clinical grid electrode system according to claim 1, wherein temperature control is implemented in a steady state mode wherein the temperature of a focal part of the brain is held at a lower temperature for several seconds or minutes.

6. The clinical grid electrode system according to claim 1, wherein temperature control is implemented in a pulse control mode, wherein a focal part of the brain is rapidly cooled using one or more brief pulses each of which will last for a few seconds to tens of seconds.

7. The clinical grid electrode system according to claim 1, wherein the control system includes a multiplexer, amplifier, A/D converter, microprocessor, infrared transceiver, antenna, power supply, external receiver, and external power transmitter.

8. The clinical grid electrode system according to claim 1, wherein the cooling sensing elements are connected to remote circuitry which is mounted within a body cavity adjacent the cooling and sensing array.

9. The clinical grid electrode system according to claim 8, wherein the remote circuitry includes a multiplexer that selects appropriate cooling sensing elements to be measured and/or activated.

10. The clinical grid electrode system according to claim 9, wherein the multiplexer is controlled by a microprocessor.

11. The clinical grid electrode system according to claim 1, wherein the cooling sensing elements are connected by an analog switch network.

12. The clinical grid electrode system according to claim 11, wherein the analog switch network creates connections between individual electrodes and functional circuitry to provide tissue stimulation current and enable remote circuitry to measure impedance.

13. A clinical grid electrode system for seizure control through local cooling, mapping brain function and the provision of reversible functional ablation comprising:
- a modular scalable cooling and sensing array composed of a plurality of cooling sensing elements, wherein each of the cooling sensing elements is composed of a cooling module, a temperature sensor and an EEG electrode; and
- a control system to which the cooling and sensing array is coupled for providing for control and monitoring of the cooling sensing elements making up the cooling and sensing array
- wherein each of cooling sensing elements has a layered configuration with a lowermost tissue contact layer composed of the EEG electrode positioned on the cooling module, a cooling plate positioned along the lowermost tissue contact layer and to which the EEG electrode is mounted.

14. The clinical grid electrode system according to claim 13, wherein a thin-film thermoelectric cooling element with a fast response time, high heat pumping capacity, and small/thin footprint is secured to a backside of the cooling plate.

15. The clinical grid electrode system according to claim 14, wherein a heat plate and a heat spreader are mounted on a side of the thin-film thermoelectric cooling element opposite the cooling plate.

16. The clinical grid electrode system according to claim 15, wherein the heat spreader is composed of a phase change material.

17. The clinical grid electrode system according to claim 13, wherein the cooling module, the temperature sensor, and the EEG electrode are mounted within a film supporting structure and the temperature sensor is mounted along the film supporting structure at a position adjacent the cooling module and the EEG electrode.

18. A cooling sensing element for an clinical grid electrode system for seizure control through local cooling, mapping brain function and provision of reversible functional ablation, comprising:
- a cooling module;
- a temperature sensor; and
- an EEG electrode;
- wherein the cooling module, the temperature sensor and the EEG electrode are mounted within a film supporting structure.

19. The cooling sensing element according to claim 18, wherein the cooling module includes a miniaturized active thermoelectric cooling element with a fast response time, high heat pumping capacity, and small/thin footprint.

20. The cooling sensing element according to claim 19, wherein the cooling module also includes a phase change material based heat spreader.

21. A cooling sensing element for an clinical grid electrode system for seizure control through local cooling, mapping brain function and provision of reversible functional ablation, comprising:
- a cooling module;
- a temperature sensor; and
- an EEG electrode;
- wherein each of the cooling sensing elements has a layered configuration with a lowermost tissue contact layer composed of the EEG electrode positioned on the cooling module, a cooling plate positioned along the lowermost tissue contact layer and to which the EEG electrode is mounted.

22. The cooling sensing element according to claim 21, wherein a thin-film thermoelectric cooling element with a fast response time, high heat pumping capacity, and small/thin footprint is secured to a backside of the cooling plate.

23. The cooling sensing element according to claim 22, wherein a heat plate and a heat spreader are mounted on a side of the thin-film thermoelectric cooling element opposite the cooling plate.

24. The cooling sensing element according to claim 22, wherein the heat spreader is composed of a phase change material.

25. The cooling sensing element according to claim 21, wherein the cooling module, the temperature sensor, and the EEG electrode are mounted within a film supporting structure and the temperature sensor is mounted along the film supporting structure at a position adjacent the cooling module and the EEG electrode.

* * * * *